United States Patent
Leon

(10) Patent No.: US 10,639,448 B2
(45) Date of Patent: May 5, 2020

(54) COGNITION AND MEMORY ENHANCEMENT VIA MULTIPLE ODORANT STIMULATION

(71) Applicant: THE REGENTS OF THE UNIVERSITY OF CALIFORNIA, Oakland, CA (US)

(72) Inventor: Michael Leon, San Juan Capistrano, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/383,186

(22) Filed: Apr. 12, 2019

(65) Prior Publication Data

US 2019/0314601 A1 Oct. 17, 2019

Related U.S. Application Data

(60) Provisional application No. 62/657,621, filed on Apr. 13, 2018.

(51) Int. Cl.
*A61M 21/02* (2006.01)
*A61M 21/00* (2006.01)
*A61B 5/00* (2006.01)

(52) U.S. Cl.
CPC ............ *A61M 21/02* (2013.01); *A61M 21/00* (2013.01); *A61B 5/4812* (2013.01); *A61M 2021/0016* (2013.01); *A61M 2205/3569* (2013.01)

(58) Field of Classification Search
CPC .......... A61M 21/02; A61M 2205/3569; A61M 2021/0016; A61B 5/4812
See application file for complete search history.

(56) References Cited

U.S. PATENT DOCUMENTS

| | | |
|---|---|---|
| 5,904,916 A | 5/1999 | Hirsch |
| 6,581,915 B2 | 6/2003 | Bartsch et al. |
| 6,950,607 B2 | 9/2005 | Yip et al. |

(Continued)

FOREIGN PATENT DOCUMENTS

| | | |
|---|---|---|
| EP | 1184083 A1 | 3/2002 |
| EP | 2125044 B1 | 1/2012 |

(Continued)

OTHER PUBLICATIONS

Sala et al. "Near and Far Transfer in Cognitive Training: A Second-Order Meta-Analysis", Collabra: Psychology, 5(1): 18. (Year: 2019).*

(Continued)

*Primary Examiner* — Kaylee R Wilson
(74) *Attorney, Agent, or Firm* — Karen S. Canady; canady + lortz LLP

(57) ABSTRACT

Disclosed herein are methods, kits, and devices for improving cognitive function and memory through olfactory stimulation. In some embodiments, olfactory stimulation is performed by releasing one or more scents according to an olfactory stimulation regimen or schedule. The methods, kits and devices described herein can provide a large impact on cognition with minimal effort and cost. They can be used widely and effectively among older adults, children, and other populations in need of improved cognitive performance.

11 Claims, 11 Drawing Sheets

(56) References Cited

U.S. PATENT DOCUMENTS

| | | |
|---|---|---|
| 7,223,361 B2 | 5/2007 | Kvietok et al. |
| 7,543,761 B2 | 6/2009 | Mehus et al. |
| 7,544,332 B2 | 6/2009 | De Silva et al. |
| 7,610,118 B2 | 10/2009 | Schramm et al. |
| 8,016,207 B2 | 9/2011 | Kvietok et al. |
| 8,061,628 B1 | 11/2011 | Kvietok et al. |
| 8,119,064 B2 | 2/2012 | Woo et al. |
| 8,210,448 B2 | 7/2012 | Kvietok et al. |
| 8,349,251 B2 | 1/2013 | Woo et al. |
| 8,382,484 B2 | 2/2013 | Wetmore et al. |
| 8,573,980 B2 | 11/2013 | Wetmore et al. |
| 8,603,398 B2 | 12/2013 | Broncano Atencia et al. |
| 8,651,395 B2 | 2/2014 | Kvietok et al. |
| 8,721,962 B2 | 5/2014 | Woo et al. |
| 8,759,275 B2 | 6/2014 | Smets et al. |
| 8,983,278 B2 | 3/2015 | Ruiz Ballesteros et al. |
| 9,327,046 B2 | 5/2016 | Turner et al. |
| 9,393,337 B2 | 7/2016 | Gruenbacher et al. |
| 9,517,286 B1 | 12/2016 | Li |
| 9,808,550 B2 | 11/2017 | Fantuzzi et al. |
| 9,839,762 B2 | 12/2017 | Berg et al. |
| 9,931,425 B2 | 4/2018 | Edwards et al. |
| 10,029,267 B2 | 7/2018 | Connolly et al. |
| D836,764 S | 12/2018 | Avidor et al. |
| 2002/0036155 A1 | 3/2002 | Freeman et al. |
| 2006/0196100 A1* | 9/2006 | Laudamiel-Pellet ............... A01M 1/2033 43/1 |
| 2013/0190556 A1* | 7/2013 | Wetmore ............... A61M 21/02 600/28 |
| 2014/0051045 A1 | 2/2014 | Stults |
| 2017/0247145 A1 | 8/2017 | Reisacher |
| 2018/0056013 A1 | 3/2018 | Knowles |
| 2018/0056028 A1 | 3/2018 | Knowles |
| 2018/0071425 A1* | 3/2018 | Jin ............... A61L 9/14 |

FOREIGN PATENT DOCUMENTS

| | | |
|---|---|---|
| WO | WO2016164917 A1 | 10/2016 |
| WO | WO2017156167 A1 | 9/2017 |

OTHER PUBLICATIONS

Linares et al. "Nearest transfer effects of working memory training: A comparison of two programs focused on working memory updating" PLoS One 14(2):e0211321 (Year: 2019).*

Sala et al. "Does Far Transfer Exist? Negative Evidence From Chess, Music, and Working Memory Training" Current Directions in Psychological Science 26(6): 515-520 (Year: 2017).*

Birte-Antina et al. "Olfactory training with older people" Int J Geriatr Psychiatry; 33:212-220 (Year: 2018).*

Moss, Mark, et al., (2008) Modulation of Cognitive Performance and Mood by Aromas of Peppermint and Ylang-Ylang, International Journal of Neuroscience, 118:1, 59-77, DOI: 10.1080/00207450601042094.

(Perfume Polytechnic) Exploring olfaction in perfume, art, science & life. Scent Mapping: Diagrams and Aroma Wheels. https://perfumepolytechnic.wordpress.com/2014/12/13/scent-mapping-diagrams-and-aroma-wheels/ Available online Dec. 13, 2014; title; pp. 2-3.

International Search Report for copending application PCT/US19/27298.

Saito, Sachiko, et al., Development of a Smell Identification Test Using a Novel Stick-Type Odor Presentation Kit, Chem. Senses 31: 379-391, 2006. doi:10.1093/chemse/bjj042.

* cited by examiner

COGNITION AND MEMORY ENHANCEMENT VIA MULTIPLE ODORANT STIMULATION

RELATED APPLICATIONS

This application claims benefit of and priority to U.S. Provisional Application Ser. No. 62/657,621 filed Apr. 13, 2018, entitled Cognition and Memory Enhancement Via Multiple Odorant Stimulation, which is hereby incorporated herein by reference in its entirety.

BACKGROUND OF THE INVENTION

Environmental enrichment has been shown to have a positive impact on cognitive function such as in ameliorating cognitive decline in various animal models. Enriching an environment can be accomplished in a variety of ways including, but not limited to, the introduction of various objects, sounds, smells, colors, animals, etc. Thousands of research papers reaching this conclusion have been published and the cognitive benefits have been shown to reduce or overcome animal models of human neurological disorders such as Alzheimer's disease, memory loss, vascular dementia, neuronal death in aging, traumatic brain injury, head injury, Parkinson's disease, seizures, stroke, multiple sclerosis, anxiety, autism, ADHD, Huntington's disease, Down Syndrome, stress, depression, cerebral palsy, chemo-brain, schizophrenia, prenatal alcohol syndrome, lead exposure, addiction and cancer, to name a few. Noticeable behavioral changes have been observed in children with autism after as little as six months of environmental enrichment exercises.

Of the various stimulants used in environmental enrichments, it has been found that cognition is strongly associate with olfaction. Olfaction is the only sense that has a large, direct pathway to the cognitive and emotional areas of the brain. Loss of olfaction precedes the memory loss from aging and from all forms of dementia. Olfactory loss triggers a massive loss of neurons in the brain. After the age of 50, it has been found that olfactory ability accurately predicts all-cause mortality within the next five years.

Biologically, olfactory stimulation activates the entorhinal cortex. The entorhinal cortex diminishes with age and other factors such as Alzheimer's and other forms of dementia. As the entorhinal cortex diminishes, it releases the dentate gyrus and CA3 (hippocampal subfields) from inhibition, thereby interfering with memory. Thus, a restoration of olfaction should increase neurogenesis and/or neural complexity in the entorhinal cortex, thereby normalizing dentate/CA3 activity and restoring memory.

Interventions based on environmental enrichment can be expensive or difficult to maintain, as in the case of exercise. Currently, there is a lack of environmental enrichment modalities that effectively improve cognitive function and memory while being low cost, and easy to use or maintain. More specifically, there is a lack of environmental enrichment modalities that exploits the strong association that olfaction has with the cognitive and emotional areas of the brain.

OBJECTS AND SUMMARY OF THE INVENTION

Provided herein are methods, kits, and devices for improving cognitive function and memory, as well as preventing loss of these functions. In some embodiments, the environment of the aging brain is improved by reversing and/or preventing the decline in sensory systems in older adults and those suffering from or at risk for neurodegenerative conditions and/or cognitive decline. In some embodiments, the cognitive outcomes of children and/or younger adults are improved. In other embodiments, the methods can be used to decrease colic in a baby, normalize premature infant brain development, decrease cognitive age in adults, and decrease or prevent migraines and headaches. The methods, kits and devices described herein can provide a large impact on cognition with minimal effort and cost. They can be used widely and effectively among older adults, children, and other populations in need of improved cognitive performance.

Generally, the present invention is directed to methods and devices for improving cognitive function in the brain by stimulating the olfactory senses. Stimulation, in most embodiments, is accomplished by subjecting a treatment recipient to unique scents on a rotating schedule of intervals. It has been found that a single, specific odor, while potentially pleasant, does not have significant cognitive benefits. However, when a treatment recipient is subjected to a daily rotation of different scents, the olfactory stimulations trigger accelerated creation of new neurons (neurogenesis), as has been shown in mice, and/or increased neural complexity, leading to oversized improvements in general cognition and memory (Far Transfer Effects), as compared to practice effects on the same task (Near Transfer Effects).

Far Transfer is the improvement in memory unrelated to practice on that specific task and it thereby improves people's general memory. Near Transfer is the ability to get better at a specific task with practice on that task, but does not result in an improvement in other cognitive abilities. There are many computer games and other activities that are advertised as brain improvement activities. These activities are all examples of Near Transfer.

One aspect of the invention maximizes the Far Transfer Effects by providing an olfactory stimulation schedule that includes a variety of odors, some of which are novel to the recipient.

Another aspect of the invention maximizes the Far Transfer Effects by providing an olfactory stimulation schedule that rotates the odors being presented to the recipient.

Still another aspect of the invention provides an olfactory stimulation schedule that provides odors that are pleasing to the recipient.

Yet another aspect of the invention provides an olfactory stimulation schedule that is delivered consistently over several months.

Treatment programs, especially those that are self-administered, or administered by a family member in the home over a prolonged period, require dedication and discipline. Understandably, the efficacy of a treatment program improves if the treatment is administered consistently. Thus, one aspect of the invention seeks to maximize the likely administration consistency by making the program as enjoyable, easy to administer, and as non-disruptive to the lifestyle of the recipient as possible. This is accomplished through "ease of use factors."

One aspect of the invention provides pleasant scents as an ease of use factor.

Another aspect of the invention is a device that creates rotating scents as an ease of use factor.

Another aspect of the invention is a device that rotates scents on a schedule as an ease of use factor.

Another aspect of the invention presents an aroma schedule automatically while a treatment recipient is sleeping as an ease of use factor.

It has been determined that while a recipient is sleeping, odors do not awaken that person. As such, a recipient will not awaken when subjected to an unpleasant odor. As such, unpleasant odors may generally be more novel to a recipient than pleasant odors. With this in mind, one aspect of the invention provides potentially unpleasant odors while the recipient is sleeping.

Another aspect of the invention provides a schedule that includes odors that are likely to be pleasing and odors that are likely to be less-pleasing, with the less-pleasing odors occurring during intervals during which the recipient will not be awake. For example, the pleasing odors will be scheduled at times when the recipient may be falling asleep, and in the morning when the recipient may be waking up. The less-traditional or potentially unpleasant odors are schedule for exposure in the middle of the night when the recipient is less likely to be awake.

Another aspect of the invention provides an identification system whereby a recipient can tag a scent as unpleasant, or give the scent a rating on a scale, and the scent delivery system thus schedules scents with the lowest rating during hours when the recipient is most likely to be asleep.

Yet another aspect of the invention tracks, over the entire treatment program, the scents that the recipient has been subjected to, in order to ensure that novelty is maintained. Through experimentation, it has been determined that a variety of scents provides the greatest efficacy. In one embodiment, at least seven embodiments are used.

In another embodiment, at least four scents are used. However, the device that provides these scents is capable of "playing" or emitting one or more of the scents simultaneously. As such, two or more base scents may be mixed together to create new scents.

In another embodiment a device is provided that can play multiple base scents simultaneously (also referred to as mixing the scents), as well as varying the intensity of each base scent. Thus, a nearly infinite number of scents may be created using only four base scents.

As one skilled in the art is aware, the sleep cycle consists of various stages that repeat every 90 to 110 minutes. One model breaks the sleep cycle into five stages: Stage 1 is light sleep characterized by a decreasing amount of muscle, brain and eye activity; Stage 2 involves a slowing of heart rate and breathing pattern, as well as a slight decrease in body temperature. Stage 3 is where deep sleep begins and involves very slow delta waves produced by the brain; Stage 4 is very deep sleep with rhythmic breathing, limited muscle activity, and continued delta wave production; and the fifth stage is called the REM (Rapid Eye Movement) stage. This is the dream stage characterized by a rise in blood pressure, heart rate, breathing rate, and rapid eye movement. It is likely that the treatment efficacy of the olfactory stimulation therapy of the invention may vary depending on which sleep stage the recipient is in. For example, it may be determined that treatment delivered during stages 3 and 4 have no effect while treatment delivered during REM is the most effective of all the stages.

With this in mind, one aspect of the invention includes a sleep stage tracking system, such as a heart rate monitor, respiration monitor, blood pressure monitor, brain wave sensor, or any combination thereof. The sleep stage tracking system is used in conjunction with the scent delivery schedule to ensure that break intervals (periods between the scent delivery intervals) occur during sleep stages that are less effective, and that scent intervals occur during sleep stages that are of maximum effectiveness.

Described herein is a method of improving at least one of cognitive function and memory by treating a subject in need thereof according to an olfactory stimulation regimen. In one embodiment, the method comprises: a) releasing one or more scents to the subject in an initial step on a first day; and b) releasing one or more scents to the subject in a later step on a later day the one or more scents in the later step are not identical to the one or more scents in the initial step, whereby at least one of cognitive function and memory of the subject is improved. In some embodiments, the method is provided in conjunction with other forms of environmental, sensorial, or tactile stimulation. In other embodiments, the olfactory stimulation is provided in the absence of tactile stimulation, or in the absence of other forms of environmental or sensorial stimulation.

In one embodiment, subjects treated with the method experience statistically improved cognitive function compared to untreated subjects as measured by Stroop test, Rey Auditory Verbal Learning Test (RAVLT), Wechsler Adult Intelligence Scale (WAIS) test, or a combination thereof. In one embodiment, the method improves or reduces age-related memory loss for the subject. In one embodiment, the memory of the subject is improved. In one embodiment, the method improves cognition, memory, intelligence quotient (IQ), or a combination thereof.

In one embodiment, the method prevents, reverses, stops, or slows progression of a neurodegenerative disease or condition. In one embodiment, the neurodegenerative disease or condition is Alzheimer's disease, Parkinson's disease, motor neuron disease, Huntington's disease, or dementia.

In one embodiment, the method improves memory, intelligence, sleeping, brain normalization, gait, balance, Alzheimer's disease, Parkinson's disease, motor neuron disease, Huntington's disease, other forms of dementia, agitation, post-traumatic stress disorder (PTSD), panic attacks, stress, generalized anxiety disorder (GAD), obsessive compulsive disorder (OCD), social anxiety disorder (SAD), phobias, depression, major depressive disorder (MDD), premenstrual syndrome (PMS), high blood pressure, colic, migraines, sleep disorder, or a combination thereof.

In one embodiment, the method improves progression or outcome for stroke rehabilitation, seizures, prenatal alcohol syndrome, lead exposure, multiple sclerosis, addiction, schizophrenia, Down Syndrome, μ-opioid receptor loss, Fragile X Syndrome, Rett Syndrome, Potocki-Lupski Syndrome, repetitive behavior, Lewy body dementia, fronterotemporal dementia, or Creutzfeldt-Jakob disease.

In one embodiment, the method decreases dementia or dementia-associated disruptive behaviors, increases self-esteem, decreases stress, decreases blood pressure, increases relaxation, prevents oxidative damage, improves postural stability, improves gait, increases deep sleep, improves mood, decreases anxiety, improves vigor, improves quality of life, improves cognition, or improves depression or depressive symptoms.

In one embodiment, the method improves cognitive processing speed, attention capacity, executive function, or a combination thereof. In one embodiment, the method improves sequential processing, mental manipulation, attention, concentration, memory span, short-term auditory memory, verbal learning and memory, sequential processing, rote learning and memory, encoding, auditory processing, working memory, transformation of information, visual-spatial imaging, or a combination thereof. In one embodiment, the method improves cognition, memory, intelligence quotient (IQ), or a combination thereof.

In one embodiment, the subject is elderly. In one embodiment, the subject has experienced age-related deficits in cognitive functions, including but not limited to, deficits in memory. In one embodiment, the subject is at least about 35, 40, 45, 50, 55, 60, 65, 70, 75, 80, 85, 90, 95, or about 100 years old. In one embodiment, the subject is an older adult, aged 55 years or older. In another embodiment, the subject is a younger adult, aged 18-55 years.

In one embodiment, the subject is a child. In some embodiments, the child is one who exhibits normal cognitive capabilities (irrespective of achievements or performance on cognitive assessments), such as a child who does not meet the criteria for a diagnosis of autism. In some embodiments, the child is a typical child who does not exhibit or experience any particular challenges to his or her environment or cognitive abilities. In some embodiments, the child has one or more developmental disorders. Representative examples of developmental disorders include, but are not limited to, autism, ADHD and developmental delay. In one embodiment, the child is autistic. In other embodiments, the child has one or more developmental disorders other than autism.

In some embodiments, the olfactory stimulation regimen is performed over a period of 2, 3, 4, 5, 6, 7, 8, 9, or 10 days. In some embodiments, the olfactory stimulation regimen is performed over a period of 2 or more days. In some embodiments, the olfactory stimulation regimen is performed over a period of at least 1, 2, 3, or 4 weeks. In some embodiments, the olfactory stimulation regimen is performed over a period of at least 1, 2, 3, 4, 5, or 6 months. In some embodiments, the olfactory stimulation regimen is performed over a period of at least 7, 8, 9, 10, 11, or 12 months. In some embodiments, the olfactory stimulation regimen is performed over a period of about 3 months. In some embodiments, the olfactory stimulation regimen is performed over a period of about 6 months.

In some embodiments, scents used in the olfactory stimulation regimen are from one or more scent categories selected from the group consisting of floral, woody, and aromatic. In some embodiments, the scents used are from two or three of these categories. Optionally, in some embodiments, additional scent categories can be used, such as oriental and/or fresh.

In some embodiments, scents used in the olfactory stimulation regimen are from one or more scent categories selected from the group consisting of fruity, flowery, woody, resinous, and aromatic. In some embodiments, the scents used are from two, three, four or all five of these categories.

In some embodiments, scents used in the olfactory stimulation regimen are selected from the group consisting of lavender, citrus, jasmine, lilac, mint, cinnamon, peppermint, cloves, lemongrass, coffee, anise, basil, thyme, chamomile, rosemary, cucumber, coconut, fresh cotton, violet, vanilla, forest pine, pomegranate, pear, orange, apple, rosehip, saffron, sage, eucalyptus, frankincense, nutmeg, and sandalwood. In some embodiments, the scents used are from any combination of two or more of these group members.

In some embodiments, steps of the olfactory stimulation regimen are performed during night time. In some embodiments, steps of the olfactory stimulation regimen are performed during day time. In some embodiments, steps of the olfactory stimulation regimen are performed during both day time and night time.

In some embodiments, the olfactory stimulation regimen is performed as a series of stimulation cycles, each stimulation cycle comprising at least two olfactory stimulation steps. In some embodiments, the olfactory stimulation regimen comprises at least one stimulation cycle comprising at least 3, 4, 5, 6, 7, 8, 9, or 10 steps. In some embodiments, the olfactory stimulation regimen comprises repeating the at least one stimulation cycle for a specified period of time. In some embodiments, the olfactory stimulation regimen comprises a stimulation cycle of 6 steps. In some embodiments, the olfactory stimulation regimen comprises a stimulation cycle of 7 steps.

In some embodiments, at least one step of the olfactory stimulation regimen comprises: a) releasing at least one scent continuously for a first duration; and b) ceasing release of the at least one scent for a second duration. In one embodiment, the first duration is about 5 minutes. In one embodiment, the second duration is about 1 minute.

In one embodiment, the at least one step further comprises repeating a) and b). In one embodiment, a) and b) are repeated until the subject has been exposed to the at least one scent for a specified exposure period. In one embodiment, the specified exposure period is about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 60 minutes. In one embodiment, the specified exposure period is up to about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 60 minutes.

In some embodiments, each step of the olfactory stimulation regimen comprises: a) releasing at least one scent continuously for a first duration; and b) ceasing release of the at least one scent for a second duration.

In some embodiments, each step of the olfactory stimulation regimen is administered using a nebulizer or diffuser. In some embodiments, each step of the olfactory stimulation regimen is administered through ventilation, heating, humidification or vaporization, nebulization or atomization of one or more scents, or a combination thereof. In some embodiments, each step of the olfactory stimulation regimen is administered using at least one candle, tea light diffuser, nebulizing diffuser, room spray, evaporative diffuser, evaporative fan diffuser, vaporizing diffuser, wearable evaporative diffuser, ultrasonic diffuser, heat evaporative diffuser, evaporative pad diffuser, cream, wick, open odorant container, or any combination thereof.

In some embodiments, at least one step of the olfactory stimulation regimen exposes the subject to one scent. In some embodiments, each step of the olfactory stimulation regimen exposes the subject to one scent. In some embodiments, at least one of the olfactory stimulation steps exposes the subject to a plurality of scents. In some embodiments, each of the olfactory stimulation steps exposes the subject to a plurality of scents.

In some embodiments, each step of the olfactory stimulation regimen exposes the subject to one or more scents for at least about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 60 minutes. In some embodiments, each step of the olfactory stimulation regimen exposes the subject to one or more scents for up to about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 60 minutes. In some embodiments, each step of the olfactory stimulation regimen comprises exposing the subject to one or more scents for about 30 minutes.

In some embodiments, the olfactory stimulation regimen comprises performing at least 2, 3, 4, or 5 steps per day. In some embodiments, the olfactory stimulation regimen comprises performing two steps per day. In one embodiment, the two steps utilize one or more scents that are identical.

In some embodiments, the olfactory stimulation regimen comprises releasing one or more scents once per day. In some embodiments, the olfactory stimulation regimen comprises consecutive steps that expose the subject to different scents. In some embodiments, the olfactory stimulation regimen comprises consecutive steps that expose the subject to identical scents.

In some embodiments, the method comprises cyclic administration of olfactory stimulation steps of the olfactory stimulation regimen. In some embodiments, the olfactory stimulation regimen comprises releasing one or more scents at least once per day. In some embodiments, the olfactory stimulation regimen comprises releasing one or more scents at least twice per day. In some embodiments, the olfactory stimulation regimen comprises daily release of one or more scents.

Also provided by the invention is a method of improving cognitive function and/or memory by treating a subject in need thereof with olfactory stimulation. In one embodiment, the method comprises: a) an earlier step exposing the subject to one or more scents; and b) a later step exposing the subject to one or more scents that are not identical to the one or more scents from the earlier step, whereby cognitive function of the subject is improved. Additionally, provided is a method of improving cognitive performance in a subject in need thereof. In one embodiment, the method comprises exposing a subject to a plurality of scents during a treatment period comprising a series of exposures at least two of the series of exposures have sets of one or more scents that are not identical.

Further provided is a method of improving cognitive performance through olfactory stimulation using a series of odorant exposure steps. In one embodiment, the method comprises an earlier odorant exposure step comprising exposing a subject to a first set of one or more odorants; and a later odorant exposure step comprising exposing the subject to a second set of one or more odorants the first set and the second set do not have identical odorants. Also provided is a method of improving cognitive function and/or memory by performing olfactory stimulation steps. In one embodiment, the method comprises exposing a subject to a first set of one or more scents; and exposing the subject to a second set of one or more scents the first set and the second set do not have identical scents.

Also provided is a method of improving cognitive function and/or memory by exposing a subject to a plurality of scents over a period of time. In one embodiment, the method comprises exposing a subject to a first set of one or more scents; and exposing the subject to a second set of one or more scents the first set and the second set have different scents.

Also provided is a method of improving cognitive function and/or memory by treating a subject in need thereof according to an olfactory stimulation regimen. In one embodiment, the method comprises a series of steps each releasing one or more scents to the subject no two consecutive steps release identical scents.

Also provided is a method of improving cognitive function and/or memory by treating a subject in need thereof according to an olfactory stimulation regimen. In one embodiment, the method comprises alternating olfactory stimulation steps each releasing one or more scents to the subject no two consecutive steps release identical scents.

Also provided is a method of improving cognitive function and/or memory by treating a subject in need thereof according to an olfactory stimulation regimen. In one embodiment, the method comprises performing one olfactory stimulation step per day, each step comprising releasing one or more scents to the subject at least once no two consecutive olfactory stimulation steps release identical scents. In one embodiment, at least one step comprises releasing one or more scents to the subject at least 2, 3, 4, 5, 6, 7, 8, 9, or 10 times. In one embodiment, each step comprises releasing one or more scents to the subject at least 2, 3, 4, 5, 6, 7, 8, 9, or 10 times.

Also provided is a method of improving cognitive function and/or memory by treating a subject in need thereof according to an olfactory stimulation regimen. In one embodiment, the method comprises: a) performing an olfactory stimulation cycle comprising a series of olfactory stimulation steps only one olfactory stimulation step is performed per day, and each step comprises releasing one or more scents to the subject at least once; and b) repeating the olfactory stimulation cycle in a). In one embodiment, further comprising repeating the olfactory stimulation cycle in a) for a specified duration.

Also provided is an olfactory stimulation kit. In one embodiment, the kit comprises: a) a scent-releasing device adapted to release a plurality of scents; b) a schedule for releasing the plurality of scents. In one embodiment, the schedule comprises: (i) releasing, from the scent-releasing device, one or more scents in an initial step on a first day; and (ii) releasing, from the scent-releasing device, one or more scents in a later step on a later day the one or more scents in the later step are not identical to the one or more scents in the initial step. In one embodiment, the schedule is provided on an instruction sheet.

In some embodiments, the plurality of scents is from one or more scent categories selected from the group consisting of floral, oriental, woody, aromatic, and fresh. In one embodiment, the plurality of scents is from one or more scent categories selected from the group consisting of floral, woody, and aromatic. In some embodiments, the plurality of scents is from one or more scent categories selected from the group consisting of fruity, flowery, woody, resinous, and aromatic. In some embodiments, the plurality of scents is selected from the group consisting of lavender, citrus, jasmine, lilac, mint, cinnamon, peppermint, cloves, lemongrass, coffee, anise, basil, thyme, chamomile, rosemary, cucumber, coconut, fresh cotton, violet, vanilla, forest pine, pomegranate, pear, orange, apple, rosehip, saffron, sage, eucalyptus, frankincense, nutmeg, and sandalwood.

In some embodiments, the schedule comprises steps performed during night time. In some embodiments, the schedule comprises steps performed during day time. In some embodiments, the schedule comprises steps performed over a period of 2, 3, 4, 5, 6, 7, 8, 9, or 10 days. In some embodiments, the schedule comprises steps performed over a period of 2 or more days. In some embodiments, the schedule comprises steps performed over a period of at least 1, 2, 3, or 4 weeks. In some embodiments, the schedule comprises steps performed over a period of at least 1, 2, 3, 4, 5, or 6 months. In some embodiments, the schedule comprises steps performed over a period of about 3 months. In some embodiments, the schedule comprises steps performed over a period of about 6 months. In some embodiments, the schedule comprises steps performed as a series of stimulation cycles, each stimulation cycle comprising at least two olfactory stimulation steps. In some embodiments, the schedule comprises at least one stimulation cycle comprising at least 3, 4, 5, 6, 7, 8, 9, or 10 steps. In some embodiments, the schedule comprises repeating the at least one stimulation cycle for a specified period of time. In some embodiments, the schedule comprises a stimulation cycle of 6 steps. In some embodiments, the schedule comprises a stimulation cycle of 7 steps.

In some embodiments, at least one step of the schedule comprises: a) releasing at least one scent continuously for a first duration; and b) ceasing release of the at least one scent for a second duration. In one embodiment, the first duration is about 5 minutes. In one embodiment, the second duration is about 1 minute. In one embodiment, the at least one step further comprises repeating a) and b). In one embodiment, a) and b) are repeated for a specified release period. In one embodiment, the specified release period is about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 60 minutes. In one embodiment, the specified exposure period is up to about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 60 minutes.

In some embodiments, each step of the schedule comprises: a) releasing at least one scent continuously for a first duration; and b) ceasing release of the at least one scent for a second duration.

In some embodiments, the scent-releasing device comprises a nebulizer or diffuser.

In some embodiments, the scent-releasing device is adapted to release the plurality of scents through ventilation, heating, humidification or vaporization, nebulization or atomization, or a combination thereof by the scent-releasing device. In some embodiments, the scent-releasing device comprises at least one candle, tea light diffuser, nebulizing diffuser, room spray, evaporative diffuser, evaporative fan diffuser, vaporizing diffuser, wearable evaporative diffuser, ultrasonic diffuser, heat evaporative diffuser, evaporative pad diffuser, cream, wick, open odorant container, or any combination thereof from the scent-releasing device.

In some embodiments, at least one step of the schedule releases one scent. In some embodiments, each step of the schedule releases one scent. In some embodiments, at least one step of the schedule releases a plurality of scents. In some embodiments, each step of the schedule releases a plurality of scents. In some embodiments, each step of the schedule releases one or more scents for at least about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 60 minutes. In some embodiments, each step of the schedule releases one or more scents for up to about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 60 minutes. In some embodiments, each step of the schedule releases one or more scents for about 30 minutes. In some embodiments, the schedule comprises releasing one or more scents at least 2, 3, 4, or 5 times per day. In some embodiments, the schedule comprises releasing one or more scents two times per day.

In one embodiment, one or more scents released on a given day are identical. In some embodiments, the schedule comprises releasing one or more scents once per day. In some embodiments, the schedule comprises consecutive steps that release different scents. In some embodiments, the schedule comprises consecutive steps that release identical scents. In some embodiments, the schedule comprises cyclic administration of olfactory stimulation steps. In some embodiments, the schedule comprises releasing one or more scents at least once per day. In some embodiments, the schedule comprises releasing one or more scents at least twice per day. In some embodiments, the schedule comprises daily release of one or more scents.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
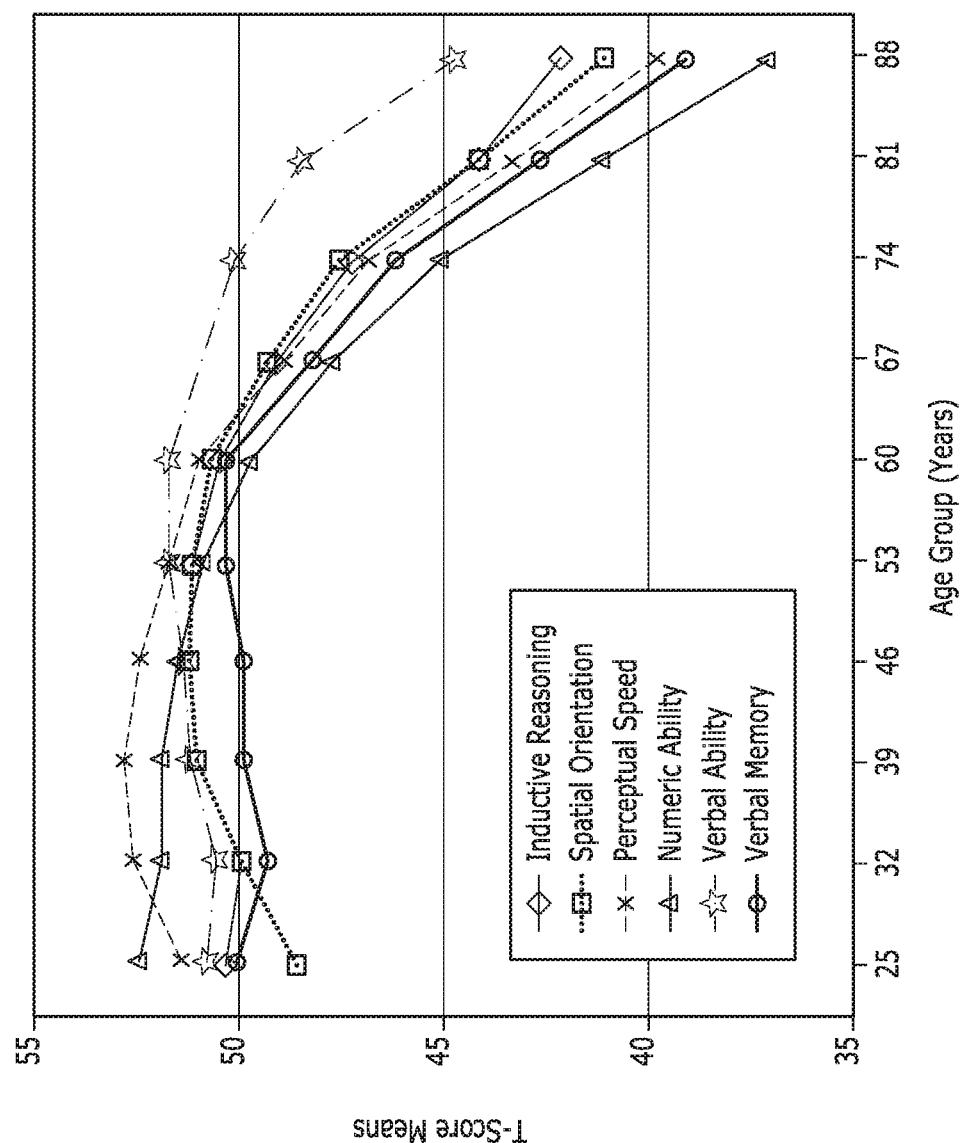
FIG. 1 is a graph showing a decline in cognitive functions over time.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

DEFINITIONS

All scientific and technical terms used in this application have meanings commonly used in the art unless otherwise specified. As used in this application, the following words or phrases have the meanings specified.

As used herein, "releasing" a scent to a subject, or "exposing" a subject to a scent, means that the scent is presented into the environment of the subject in a manner sufficient for stimulation of the subject's olfactory system.

As used herein, "decreases" or "increases" means reduces or raises, respectively, by a detectable or noticeable amount. In some embodiments, such a decrease or increase is measured using one of the assessment tools described herein. In some embodiments, the decrease or increase represents a "significant difference".

As used herein, "improves" means results in an improved state, for example, the amelioration of symptoms of an adverse condition, or the enhancement of a desired condition, such as memory.

As used herein, a "significant difference" or "significantly different" means a difference that can be detected in a manner that is considered reliable by one skilled in the art, such as a statistically significant difference, or a difference that is of sufficient magnitude that, under the circumstances, can be detected with a reasonable level of reliability. In one example, an increase or decrease of 10% relative to a reference value is a significant difference. In other examples, an increase or decrease of 20%, 30%, 40%, or 50% relative to the reference value is considered a significant difference. In yet another example, an increase of two-fold relative to a reference value is considered significant. The reference value can be, for example, an untreated subject, or a baseline (pretreatment) value for the same subject.

As used herein, ranges and amounts can be expressed as "about" a particular value or range. About also includes the exact amount. Hence "about 5 minutes" means "about 5 minutes" and also "5 minutes." Generally, the term "about" includes an amount that is from 10% below to 10% above the particular value or range. For example, "about 10 minutes" means "from 9 minutes to 11 minutes."

As used herein, "a" or "an" means at least one, unless clearly indicated otherwise.

Environmental Enrichment

In more than a dozen animal models of human neurological conditions, environmental enrichment has been shown to ameliorate their human-like symptoms, including the cognitive decline in aging (Patel, et al., 2012; Segovia, et al., 2006; Valero, et al., 2007) and in Alzheimer's disease (Arendash, et al., 2004; Arranz, et al., 2011; Basak, et al., 2008; Berardi, et al., 2007; Costa, et al., 2007; Jankowsky, et al., 2015; Lazarov, et al., 2005; Polito, et al., 2014). In humans, environmental enrichment, including exercise, computer games, social behavior and nutrition have been shown to reduce the risk of cognitive decline in aging and disease (Herzog, et al., 2008; Kirk-Sanchez and McGough, 2014; Klimova, 2016; Williams and Kemper, 2010), but it has been difficult to show that cognitive decline can be reversed, and when there are such improvements, the effects tend to be modest in size (Herzog, et al., 2008; Rodakowski, et al., 2015). Moreover, it has been shown to be difficult to keep people on such interventions as a routine program of physical exercise (Williams, et al., 2007).

The olfactory system experiences a clear deterioration in older adults, with 18% of older adults having olfactory impairment and 46% of those over 80 years old having very limited olfactory ability (Doty, et al., 1984; Hoffman, et al., 1998; Liu, et al., 2016; Murphy, et al., 2002; Pinto, et al., 2015; Toussaint, et al., 2015). The initiation of this decline parallels that seen for cognitive ability in older adults (Park, et al., 2003; Salthouse, 2009). The decline in cognitive function with age is illustrated in FIG. 1, which shows an initial decline around the age of 60 that continues as the individual ages with inductive reasoning, spatial orientation, perceptual speed, numeric ability, verbal ability, and verbal memory all being affected. The olfactory system has direct projections to cognitive areas, unlike other sensory systems, and the loss or compromise of the olfaction system results in massive volume loss in these cognitive areas in humans at any age (Bitter, et al., 2010a; 2010b; 2011; Yao, et al., 2014). Normal human aging is accompanied by a deterioration of olfactory abilities (Dong, et al., 2017; Hoffman, et al., 2016; Seubert, et al. 2017), along with the deterioration of olfactory projection sites, which include the cognitive areas of the brain (Kollndorfer, et al., 2015; Segura, et al., 2013). Moreover, a degradation of olfactory ability predicts both an elevated risk of minimal cognitive impairment (MCI) and which of those with MCI will go on the develop Alzheimer's disease (Adams, et al., 2017; Devanand, et al., 2000; Lafaille-Magnan, et al., 2017; Peter, et al., 2003; Roberts, et al., 2016; Schubert, et al., 2008; 2017; Swan and Carmelli, 2002). Remarkably, olfactory function also predicts all-cause mortality in older adults (Gopinath, et al., 2011; Pinto, et al., 2014).

The loss of olfactory function precedes or parallels the initiation of a variety of cognitive disorders such as Alzheimer's disease, Parkinson's disease, Lewy body dementia, fronterotemporal dementia, Creutzfeldt-Jakob disease, minimal cognitive impairment, and schizophrenia (Conti, et al., 2013; Devanand, et al., 2000; Devanand, et al., 2010; Doty, et al., 1988; Li, et al., 2010; Luzzi, et al., 2007; Meusel, et al., 2010; Nguyen, et al., 2010; Parrao, et al., 2012; Ponson, et al., 2004; Ross, et al., 2006; Tabaton, et al., 2004; Wattendorf, et al., 2009). Given that these cognitive disorders have widely differing etiologies, it raises the possibility that the loss of olfactory stimulation contributes to the decline in cognitive ability in each of these disorders.

In humans who have experienced olfactory loss due to a variety of problems, such as post-infectious olfactory dysfunction, head trauma, Parkinson's, and aging) increased olfactory experiences has been shown to improve olfactory identification, olfactory discrimination, and to lesser extent, olfactory threshold (Damm, et al., 2014; Geißler, et al., 2014; Haehner, et al., 2013; Hummel, et al., 2009; Konstantinidis, et al., 2013; Patel, et al., 2017). These results were achieved through exposure to four odorants taken from each of four odor groups: resinous (eucalyptus), flowery (rose), fruity (lemon), and aromatic (clove). There are further improvements in olfactory ability with increased duration of exposure, increased concentration of the odorants and an increased number of odorants (Altundag, et al., 2015; Damm, et al., 2014; Konstantinidis, et al., 2016). In addition to improvements in sensory ability, older adults exposed to increased olfactory stimulation have an improvement in their cognitive function, as evidenced by increased verbal fluency, an improvement in their depressive symptoms, and an improved sense of wellbeing (Wegener, et al., 2018).

Olfactory stimulation in older adults also decreases falls in this group (Sakamoto, et al., 2012).

Individuals with autism have olfactory dysfunction, both with their abnormal sniff response to odors of different valences (Rozenkrantz, et al., 2015) and to social odors (Endevelt-Shapira, et al. 2018). They also have abnormal olfactory responses (Boudjarane, et al., 2017; Tonacci, et al., 2017). Diverse rodent models of autism have their human-like symptoms of this disorder ameliorated when they are placed into an enriched environment (Kerr, et al., 2010; Kondo et al., 2008; Lacaria, et al., 2012; Lonetti et al., 2010; Nag et al., 2009; Restivo et al., 2005; Reynolds, et al., 2013; Schneider & Przewlocki, 2005; Schneider et al., 2006).

Environmental enrichment, which included olfactory stimulation that was paired with tactile stimulation has been successfully used to treat children with classic autism (Woo and Leon, 2013, Woo, et al., 2015). In two randomized clinical trials, parents delivered novel multisensory stimulation, featuring olfactory stimulation, each morning and evening for 15-30 min over the course of six months. 42% of the enriched children had a major improvement in their symptoms as measured on the subjective Childhood Autism Rating Scale, compared to 7% of the standard-care controls who had that kind of improvement. IQ increased by more than 8 points for enriched children, compared to about a point of improvement in controls. The Short Sensory Profile revealed an 11-point improvement for enriched children and about a point for controls. Receptive language, as measured by the objective Reynell Developmental Language Scales, improved by more than 200% in enriched with autism and less than 20% for controls. Finally, after 6 months, 21% of the children with autism were considered to have lost that diagnosis using the objective Autism Diagnostic Observation Schedule and no control child reached that level of improvement.

A review of the outcomes of over 1,000 children along the entire autism spectrum who were being given this treatment at home (Aronoff, et al., 2016) revealed that these children did better than those in the university clinical trials, with an effect size of 1.85. Not only did the core symptoms of autism improve, but the co-morbid symptoms, which accompany virtually every child with this disorder have, including: sensory processing, self-awareness, communication, mood, sleeping, eating, motor skills, learning, memory, anxiety and attention span. This treatment had similar effects on children across the entire autism spectrum, both girls and boys improved equally, and the treatment worked for all ages tested (2-18 years old). There was also a dose/response outcome for parental compliance and the symptom improvement of their children.

Schedules

Figure 2:
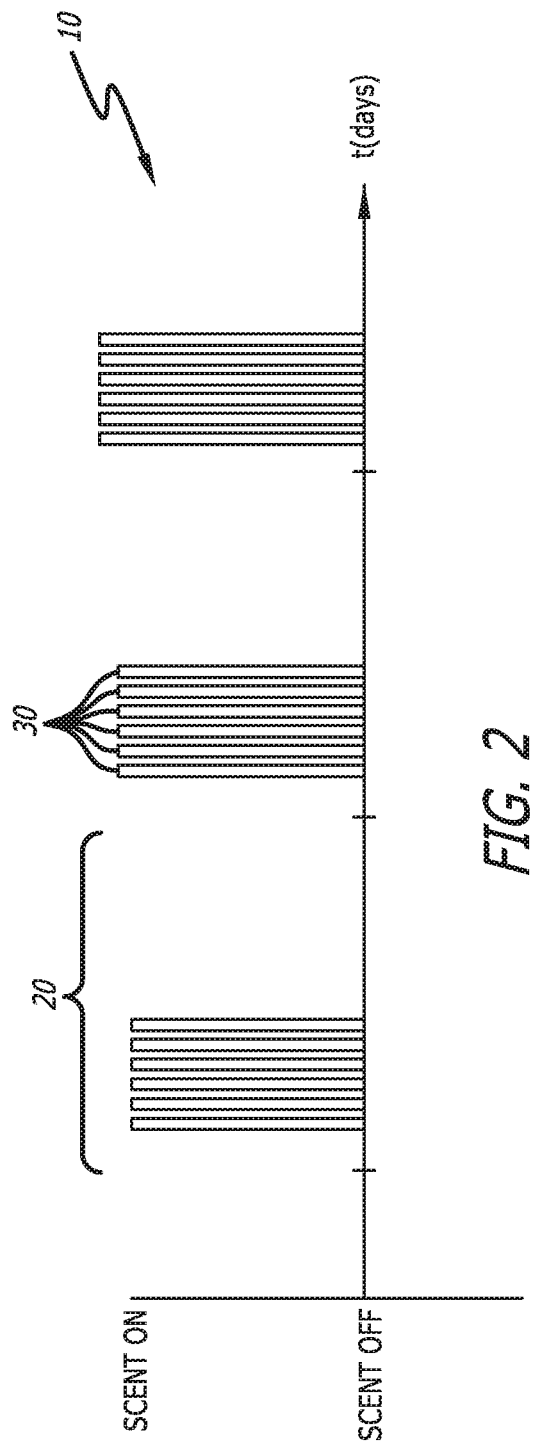
FIG. 2 is a timeline depicting the administration of an embodiment of a method of the invention.
Figure 3:
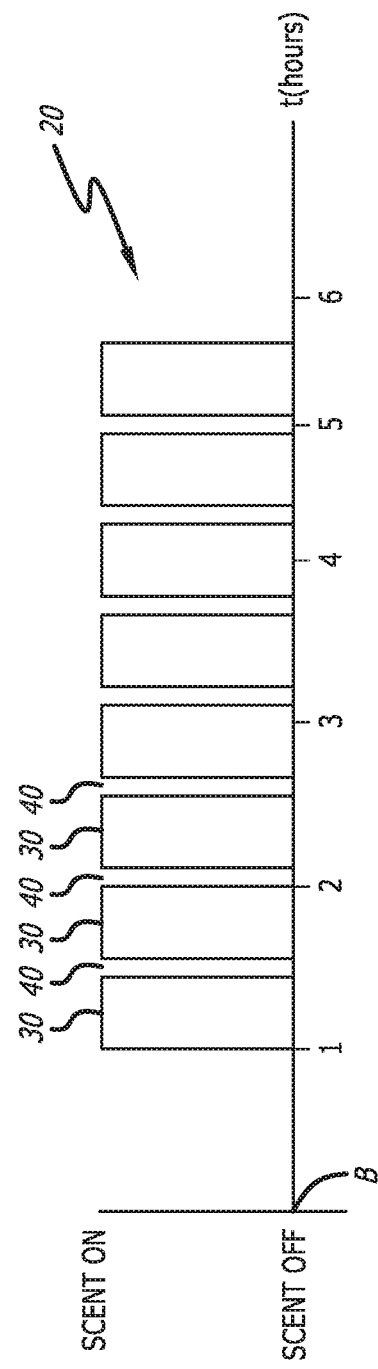
FIG. 3 is a timeline depicting an embodiment of a daily schedule of a method of the invention.

Referring now to the Figures, and first to FIGS. 2 and 3, there is shown a general illustration of a method 10 of the invention. The method 10 generally involves subjecting a treatment recipient to a daily schedule 20 of scent intervals 30 separated by breaks 40. The daily schedule is administered for several days, weeks, months or years, depending on the treatment recipient and the desired results. As there are no negative side-effects or downsides to the treatment method 10, other than perhaps the expense of the fragrances, a benefit may be found in continuing the schedule 20 indefinitely.

FIG. 3 provides a non-limiting example of a daily schedule 20 that is initiated upon bedtime B. Bedtime is selected due to the ease with which the treatment may be delivered to a person not moving around, and the effectiveness which a scent may be delivered to a person in a relatively-small, enclosed room, such as a bedroom. It is noted however that treatment effectiveness may not be diminished if the treatment is delivered during the day, such as to a person sitting at a computer, driving a vehicle, or is otherwise stationary relative to the delivery device; or if the delivery device moves with the recipient throughout the recipient's daily activities, such as would be the case with a wearable device.

In the embodiment of FIG. 3, the recipient activates a scent-delivery device (detailed below) that includes a timer that is set to deliver various odors at predetermined intervals. In this example, the intervals 30 are approximately 30 minutes long and are separated by breaks 40 that are 5 minutes in duration. It is to be understood, however, that these interval times and break times are merely non-limiting examples and may vary based on recipient preference, subjective results, doctor recommendations based on empirical evidence, sleep duration, etc. Good results have been attained with 30 minute intervals with 5 minute breaks, as a starting point.

The daily schedule 20 begins each day at a start event. For recipients with a regular daily routine, the start event may be a set time of day, rather than being initiated at bedtime. For example, in this embodiment, the first interval 30 of the daily schedule 20 may begin at midnight and continue until 12:30 am. The first break 40 thus spans from 12:30 to 12:35 am and the second interval 30 begins at 12:35 am and lasts until 1:05 am. These intervals 30 and breaks repeat this pattern until a predetermined number N of intervals 30 and breaks 40 have occurred. The number N, like the interval 30 length, may be varied based on the length of sleep the recipient typically gets, as well as subjective or objective results. Generally, N should be at least 3 for optimal results.

Figure 4:
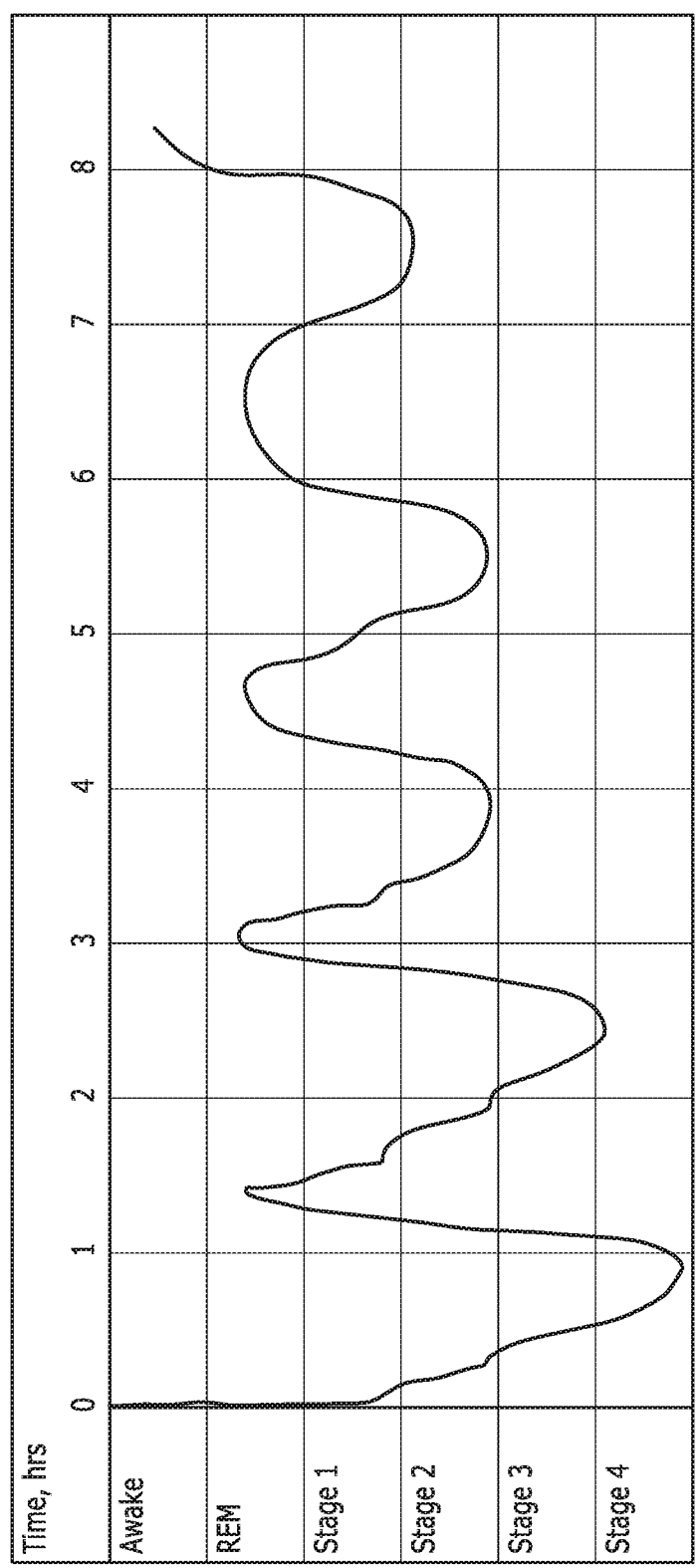
FIG. 4 is a graph showing a human sleep cycle.

In another embodiment, the start event may be tied to the sleep cycle of the recipient. FIG. 4 is a diagram of the human sleep cycle 50. The sleep cycle 50 consists of various stages that repeat every 90 to 110 minutes. One model breaks the sleep cycle into five stages: Stage 1 is light sleep characterized by a decreasing amount of muscle, brain and eye activity; Stage 2 involves a slowing of heart rate and breathing pattern, as well as a slight decrease in body temperature. Stage 3 is where deep sleep begins and involves very slow delta waves produced by the brain; Stage 4 is very deep sleep with rhythmic breathing, limited muscle activity, and continued delta wave production; and the fifth stage is called the REM (Rapid Eye Movement) stage. This is the dream stage characterized by a rise in blood pressure, heart rate, breathing rate, and rapid eye movement.

Referring again to FIG. 4, it is shown that the sleep cycle begins in stage 1 and quickly progresses to stage 4 within the first hour of falling asleep. After an hour or so, the heart rate, blood pressure, and breathing rate increase rapidly as the person enters REM sleep, which typically lasts only about 5 minutes. After REM sleep, the cycle repeats to a certain extent.

Notably, throughout the night, the degree to which the sleeper enters deep sleep diminishes. For example, as seen in the graph of FIG. 4, during the second cycle, stage 4 is barely attained. The end of the second cycle is also marked by a REM stage that lasts 10 minutes, rather than 5 minutes. The third cycle only drops into stage 2 sleep, followed by a 15 minute REM stage. The fourth cycle also only drops into stage 2 sleep and is followed by a REM stage that lasts 30-60 minutes.

Much is still to be learned about the human sleep cycle. Scientists have often thought that experiences and lessons are converted into long term memory during sleep, and further that REM sleep plays an essential role in the acquisition of learned material, both declarative and procedural memory, both forms of Near Transfer. Researchers recently have begun to hypothesize that deep, restorative sleep, also referred to as "slow-wave sleep (SWS)" plays a significant role in declarative memory by processing and consolidating newly acquired information.

With this in mind, one aspect of the invention includes a sleep stage tracking system, such as a heart rate monitor, respiration monitor, blood pressure monitor, brain wave sensor, or any combination thereof. The sleep stage tracking system is used in conjunction with the scent delivery schedule to ensure that break intervals (periods between the scent delivery intervals) occur during sleep stages that are less effective, and that scent intervals occur during sleep stages that are of maximum effectiveness. It is likely that the treatment efficacy of the olfactory stimulation therapy of the invention may vary depending on which sleep stage the recipient is in. For example, it may be determined that treatment delivered during stages 3 and 4 have no effect while treatment delivered during REM is the most effective of all the stages.

Given that there would likely be no degradation in effectiveness if a scent were to be delivered during a point in the sleep cycle that is not optimal for Far Transfer, the benefit of tracking the sleep cycle may be to simply avoid the occurrence of breaks 40 that during periods of peak Far Transfer Effects. For example, if it is determined that REM sleep is the best stage of the sleep cycle for Far Transfer Effects, it may be beneficial to avoid breaks 40 during the REM stages, especially the first two to three REM stages, which last only 5-15 minutes.

Similarly, if it is determined that Stage 4 is the most beneficial time for olfactory stimulation to be administered, it would be important to ensure that intervals 30 are scheduled during the first two sleep cycles, as the first two cycles are typically the only cycles in which Stage 4 is entered.

One embodiment of the method of the invention provides intervals 30 that coincide with the sleep cycles through the use of monitoring. Because the sleep cycles coincide with variations in biological factors such as blood pressure, heart rate, respiration rate, brain wave activity, and eye movement, one skilled in the art would realize that a number of technologies exist to monitor the various sleep stages. As such, the interval 30 durations and break 40 durations could be selected to synchronize with the sleep cycles. In this embodiment, there are as few as 3 intervals or as many as 6 or 7 intervals, depending on the length of sleep by the recipient.

One embodiment of this synchronized method involves recording the sleep patterns of the recipient over a period of days to establish a typical pattern. The delivery device is then scheduled to approximate a synchronized schedule. Under this method, the recipient would not have to use a monitoring device unless recalibration is desired.

Another embodiment of this synchronized method involves continuous monitoring of one or more of the above-mentioned biological factors. For example, heart rate monitors are common in many forms including, but not limited to, optical wearables, chest straps, air-bed pulse detectors, and the like. The biological factor is monitored continuously and the sleep cycle is determined based on the data collected therefrom. The device then activates and deactivates the various scents according to a schedule that is created based on the data. As such, the schedule may differ slightly from evening to evening. This method may be optimally suited to recipients that have a varying daily routine.

Rotations

One aspect of the invention is that the scents being delivered to the recipients be novel. This is not to imply that the scent is completely unfamiliar to the recipient over his or her lifetime, but simply that the scent changes each interval and is not re-introduced for a predetermined number of intervals. In one embodiment, at least seven different scents are used, and no scent is repeated until the other six scents have been used. In other embodiments, a vast number of scents are used such that it is unlikely that a scent would be used twice during an entire treatment program.

As a general guideline, it is believed that the more novel a scent is, the greater impact it will have. Additionally, it is believed that consecutive scents should differ as much as possible during a particular daily schedule 20. In order to achieve this, one embodiment provides a rotation that avoids placing two aromas from a same scent group adjacent to each other.

Scents are sometimes classified into scent groups, commonly referred to as the fragrance wheel or chart. There are many different fragrance charts. One widely used chart, used herein merely as an example, was developed by perfumery taxonomist Michael Edwards in 1992, and modified several times since. The 2010 version of the Michael Edwards fragrance wheel is provided as FIG. 4 and was published in 2011 in Fragrances of the World, by Michael Edwards & Co., incorporated by reference herein.

Figure 5:
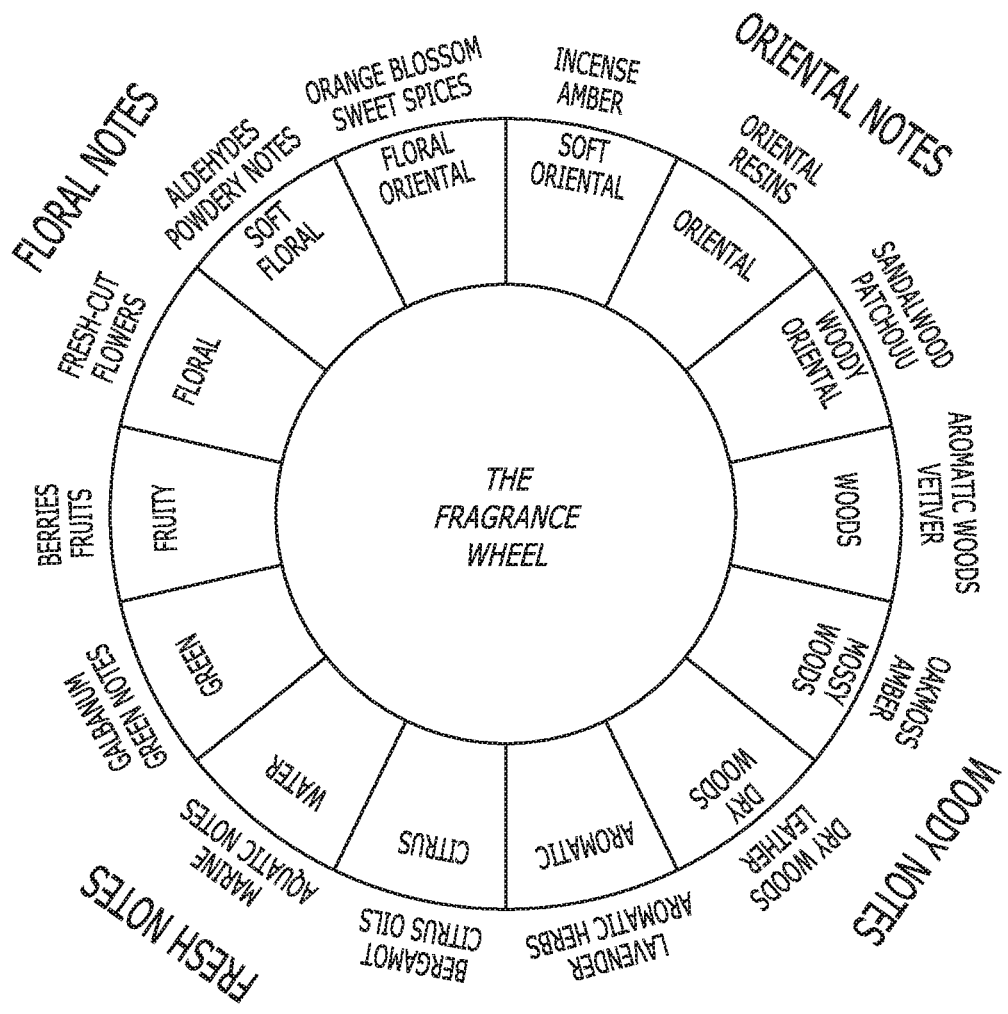
FIG. 5 is a diagram of a fragrance wheel.

As seen in FIG. 5, there are four main fragrance families: floral, oriental, woody and fresh. These are divided into sub-groups and arranged such that the sub-groups show relationship to each other. For example, the floral family is divided into floral, sort floral and floral oriental. The oriental family is divided into soft oriental, oriental and woody oriental. The floral oriental sub group from the floral oriental family is arranged next to the soft orient sub group from the oriental family because these two are the most similar, despite being in different families.

The fragrance wheel of FIG. 5 is useful because the further scent differences are easily visualized by their respective proximity on the wheel. For example, scents from the mossy woods sub group are found opposite the scents from the floral sub group. Thus, it is easy to assess that the brain will process an amber smell as very different from a fresh-cut flower smell.

In creating a rotation, a guideline for scent variety can be established using the fragrance wheel of FIG. 5. For example, a spacing of 1-5 subgroups between consecutive scents can maximize the effectiveness of the olfactory stimulation schedule 20. Similarly, it can be determined that during the course of a single daily schedule 20, at least one fragrance from each of the four families should be represented.

Figure 6:
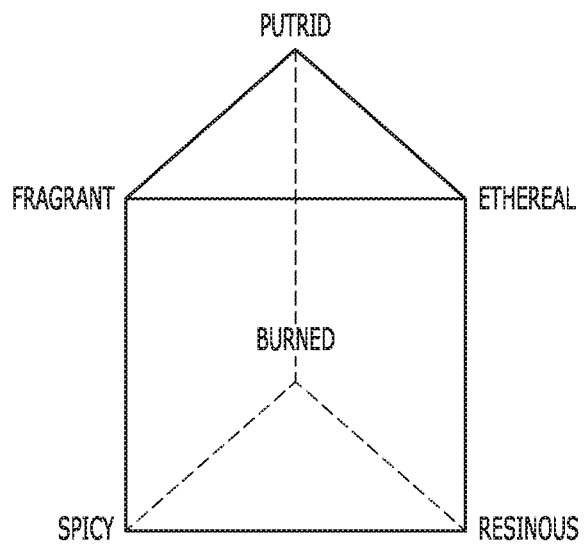
FIG. 6 is a chart showing an embodiment of a scent rotation of the invention.

FIG. 6 provides an example rotation 60 in which there is at least one sub group separating consecutive intervals 30, and all four families are represented over the seven intervals 30 of the schedule 20.

Figure 7:
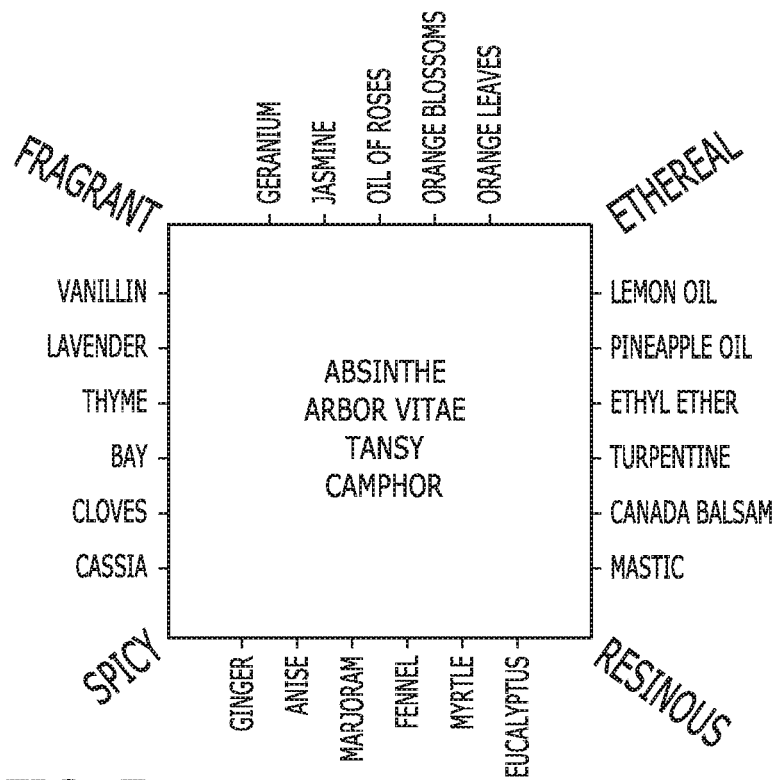
FIG. 7 is a diagram showing Henning's Prism.
Figure 8:
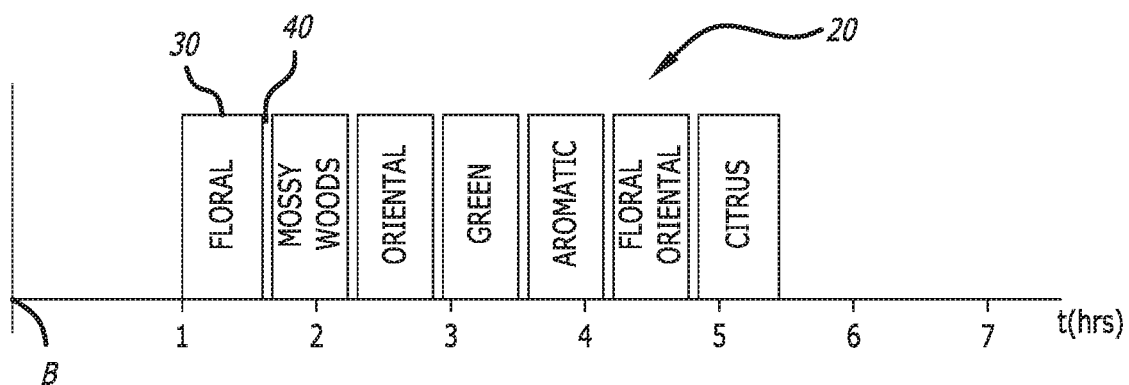
FIG. 8 is a diagram of a fragrance wheel formed from one side of Henning's Prism.

FIG. 7 provides another example of a fragrance schematic developed by Hans Henning, a German psychologist, in 1916. Henning H (1916) Der Geruch. Leipzig, Germany. The schematic of FIG. 7 is known as Henning's Prism, and is a three-dimensional prism consisting of three rectangular faces, each of which could be used as a fragrance wheel. The corners of the prism include the fragrance families: fragrant (flowery or floral), ethereal (fruity), putrid, resinous, burned, and spicy. Each face shares two families with an adjoining face. Thus, one face of the prism includes the families: flowery, fruity, spicy and resinous. Another face includes the families: flowery, spicy, burnt and putrid. The third face includes the families: burnt, putrid, fruity and resinous. Because the putrid and burnt families are generally less desirable, it is thought that the face shown in FIG. 8 will be preferred. FIG. 8 takes this face and forms a wheel including the subgroups between the families.

Intensity

The strength or intensity of the aroma being produced during the treatment must be strong enough to have an effect on the treatment recipient, but not so strong as to create lingering odors in the furniture or other objects in the room where the treatment is being administered. Optimally, the scent being delivered during each interval 30 will dissipate during the break 40 between the intervals 30. Interestingly, are not affected by scents while they sleep, so the scent being strong enough to interrupt sleep patterns is not a concern. However, as discussed above, olfaction loss occurs with age and should strengthen with treatment. As such, it is an embodiment of the invention to adjust the intensity level prior to the treatment program to a level that is easily detected by the recipient without being overpowering.

Another embodiment of the invention includes a device that allows fragrances to be mixed by "playing" two or more cartridges simultaneously. The device also allows the intensity of each scent cartridge to be adjusted by increasing or decreasing the airflow passing through the cartridge. In this way, the "recipes" may be altered by not only adjusting which cartridges are being played, but by adjusting the intensities of each cartridge that is being played. For example, if a "recipe" involves a mixture of cherry and vanilla, the cherry cartridge could be played at a 50% intensity, while the vanilla cartridge could be played at 10% intensity. This would create a different scent that if the vanilla were played at 50% and the cherry were played at 10%, for example.

Devices

A variety of devices are envisioned that could be used to practice the method 10 of the invention. These devices can generally be broken down into two categories—forced air devices and evaporative devices. The forced air devices generally include one or more scent cartridges that are engaged with a machine that pumps air, via one or more fans, bellows, turbine(s), etc., through the cartridge, preferably at a selectable rate such that intensity may be varied. Some embodiments include a plurality of cartridges on a selectable carousel that plays one cartridge at a time. Other devices include a plurality of cartridge engagement assemblies, or "play heads" to allow the cartridges to be played simultaneously.

The evaporative devices involve scent cartridges, pads or gels that are either contained within a dispensing device, or may be layered such that, once opened, an exposed layer having a first scent begins to evaporate, thereby emitting the first scent. The scent layers may be separated by odorless layers to provide breaks 40 between the scent intervals 30. The dispensing device may have mechanized covers that selectively cover and uncover a scent cartridge or may have heaters associated with each scent cartridge that raises the temperature of the gel to a point that evaporation occurs.

Figure 9:
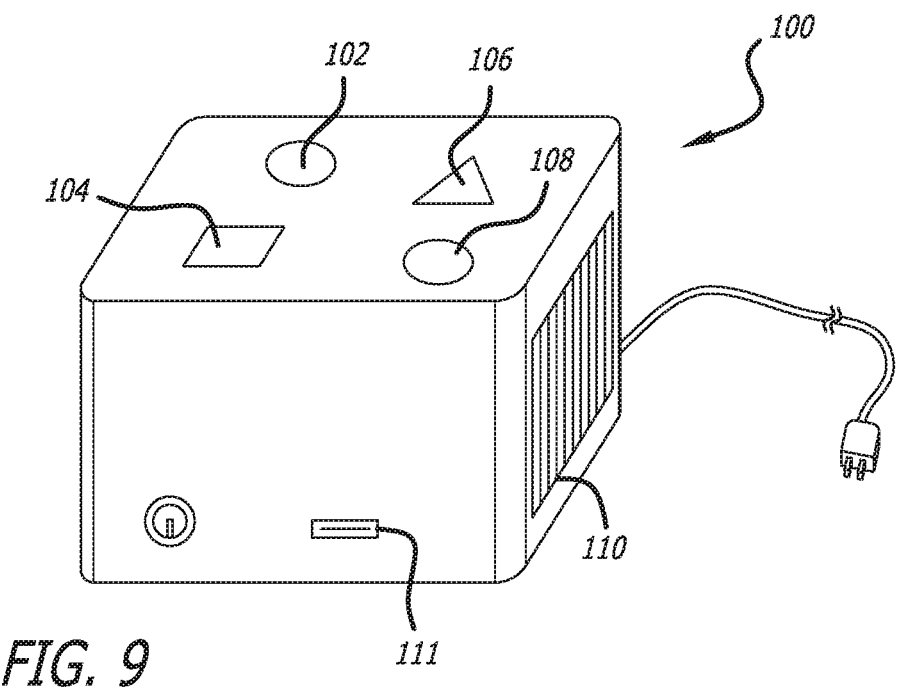
FIG. 9 is a perspective view of an embodiment of a device of the invention.

Referring now to FIG. 9, there is shown a first embodiment of a device 100 of the invention. Device 100 is a forced air device that accommodates four cartridges 102, 104, 106 and 108. Each of the cartridges may be a disposable device that allows air to flow through the cartridge to emit a fragrance. Alternatively, in the interest of ecology and cost, the cartridges may be refillable and reusable. More detail about the individual cartridges will be provided below.

Figure 10:
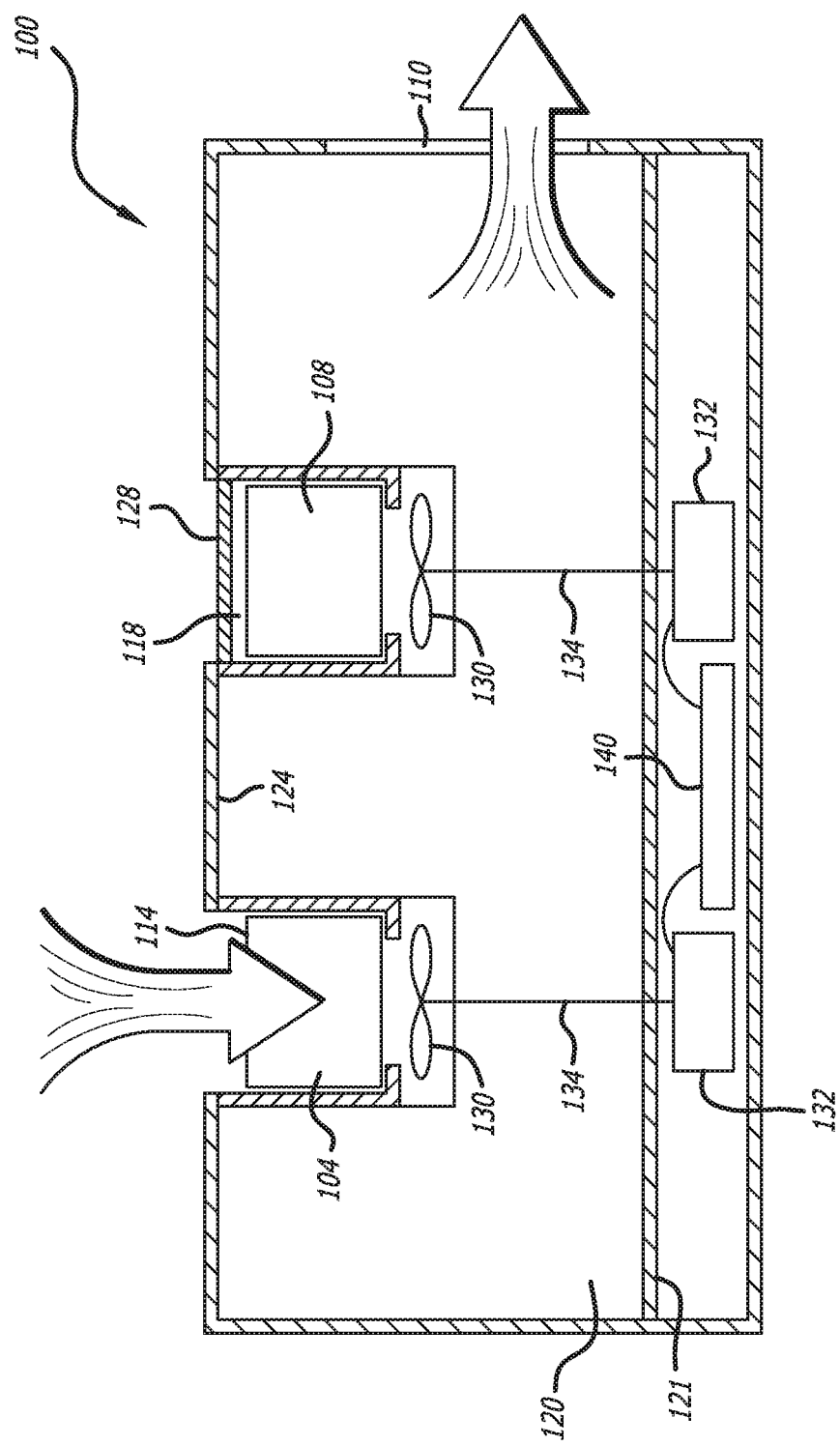
FIG. 10 is a cutaway view of the embodiment of the device of FIG. 9.

Referring to both FIGS. 9 and 10, an embodiment of the device 100 includes a housing 110 with cavities 112, 114, 116 and 118 sized and shaped to accommodate cartridges 102, 104, 106 and 108, respectively. Each cavity 112, 114, 116 and 118 may be equipped with a retractable cover 122, 124, 126 and 128, respectively, such that the cartridges not being used are preserved and aromas therefrom are not deployed.

It is envisioned that each of the cartridges and corresponding cartridges have a unique shape corresponding to a fragrance family. In this way, a recipient will be required to place a cartridge belonging to each fragrance family in the device 100. In the example of device 100, the shapes selected are circle, square, triangle and oval for cartridges 102, 104, 106 and 108. Alternatively, each cartridge could be coded, and each cavity could be equipped with a code reader such that the device 100 knows which fragrance is inserted into each cavity.

The housing has a vent 110 formed in one wall through which the fragrance from the cartridges is emitted. The sidewall was selected as most users will place the device 100 on a bedside table. The vent 110 may then be situated such that it faces the recipient.

Internally, the device includes a fan or fans 130 situated beneath the cavities. The fan 130 is powered by a motor 132 and is connected to the motor with a shaft 134. A control board 140 drives the logics that activate and deactivate each motor along with logic functions discussed in detail below. In the embodiment having one fan, flow through the individual cartridges is controlled by the covers 122, 124, 126 and 128.

The device 100 is shown as drawing air downward through the cartridges and into a central housing cavity 120. The air is forced to exit through the vent 110 because the vent 110 is the only exit for the cavity, considering that the covers are closed on cavities not being used and that fans are running on each cavity with an open cover. This design allows the central housing cavity 120 to be used as a mixing chamber in the event that more than one fragrance cartridge is being used simultaneously. In order to protect the electronic componentry, such as the motors 132 and the control board 140, a barrier 121 is provided, insulating these components from the central housing cavity 120.

One skilled in the art will realize that the device 100 may be designed such that air flow is reversed, without departing from the spirit of the invention. A reversed air flow could be accomplished by merely reversing the direction of the fans 130. This design may be advantageous in that there would be less risk of residue building up in the cavity 120.

The control board 140 is electrically connected to the fan motors 132 and includes a wireless connection technology, such as Bluetooth® that can be connected to an electronic device such as a smart phone or reader. An application, downloadable onto the device, includes control logics that allow a user to customize a treatment schedule. Alternatively, a physician may create a schedule 20 that is downloadable by the user.

The application provides various controls and options that may be incorporated into the daily schedule, including scent rotation, intensity, timing, reminders, scent shuffle, and the like. The application preferably tracks the scent rotation to assess which scents may have been played repeatedly over the course of the treatment program. These scents can be marked by the application as losing novelty and can thus be taken out of the rotation, or mixed with another scent the next time they are used.

The application can be wirelessly connected to a variety of biometric sensors listed above, such that the schedule becomes dynamically-timed. For example, the user may don a heart rate monitor when going to bed. The activation of the heart rate monitor is sensed by the application and the application begins to monitor the sleep stage of the user to determine the timing of the daily schedule 20, as discussed above.

Alternatively, if a biometric sensor is not used, the hand-held electronic device itself could be used by the control board to indicate the beginning of a daily schedule 20. For example, the device 100 may include a USB charging port 111 that is connected to the control board. The user could use this USB port to charge their phone during the evening. Plugging the phone into the device 100 could be used as an indication that the daily schedule 20 should commence. Ease of use is thus maximized as the disruption in routine is minimized, as most people are accustomed to charging their smart phones in the evening.

The control board 140 is also used to track the usage of the cartridges. Depending on the construction of the cartridge, the application can be used to provide indications to the user that a particular cartridge needs to be replaced.

Figure 11:
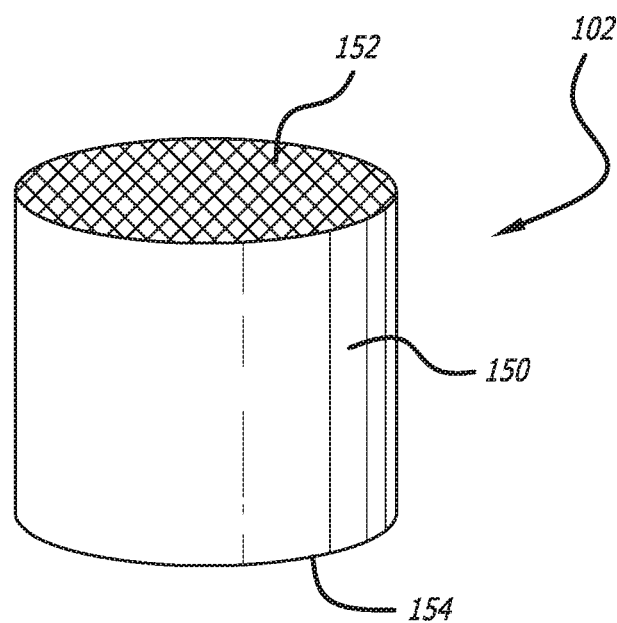
FIG. 11 is a perspective view of an embodiment of a cartridge of the invention.

FIG. 11 shows an embodiment of a cartridge 102 of the invention. This embodiment is a disposable embodiment and includes a housing 150 with a top 152 and a bottom 154. The top 152 and bottom 154 are vented such that air may pass through. The cartridge 102 would be shipped with a removable film (not shown) covering the top 152 and bottom 154 until the cartridge is ready to be used, thus preserving the odorant contained therein.

Figure 12:
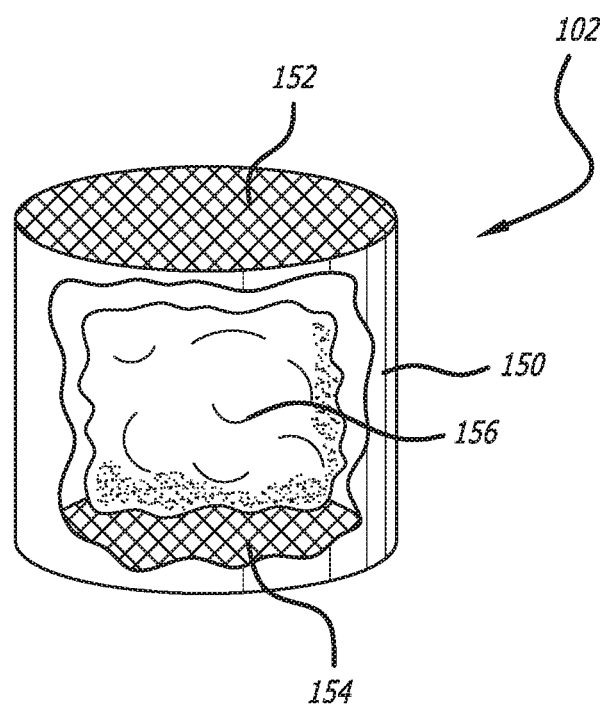
FIG. 12 is a cutaway view of the cartridge of FIG. 11.
Figure 13:
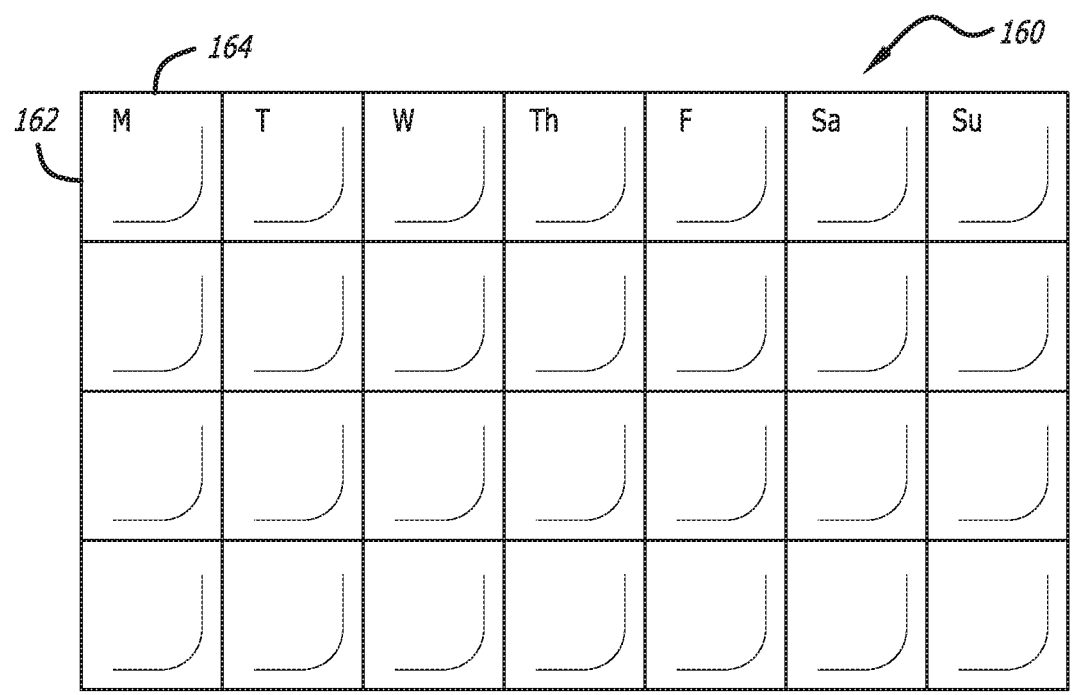
FIG. 13 is an elevation of an embodiment of a scent pad package of the invention.

FIG. 12 shows a cutaway view of the cartridge 102, allowing an absorbent odorant pad 156 to be seen. The pad 156 may be formed as a wad, such as a cotton ball or polyester fiberfill wad, and should be loosely packed such that air may flow through it. Alternatively, the pad 156 may be slightly smaller than an interior of the cartridge such that air may flow around the pad 156. In this embodiment, a denser wadding material may be used that might hold more odorant than an embodiment that requires the air to flow through the pad 156.

In one embodiment of the cartridge 150 of FIG. 12, the top 152 is removable and replaceable. This embodiment reduces plastic waste and costs. Rather than replacing the entire cartridge, odorant pads 156 could be provided or sold individually or in packages containing multiple packages. FIG. 10 shows a package 160 of pads 156 arranged such that each row 162 represents a different scent family and each column 164 thus represents a different day of the week.

As introduced above, one aspect of the invention provides evaporative devices that involve scent cartridges, pads or gels that are either contained within a dispensing device, or may be layered such that, once opened, an exposed layer having a first scent begins to evaporate, thereby emitting the first scent. The scent layers may be separated by odorless layers to provide breaks 40 between the scent intervals 30.

Figure 14:
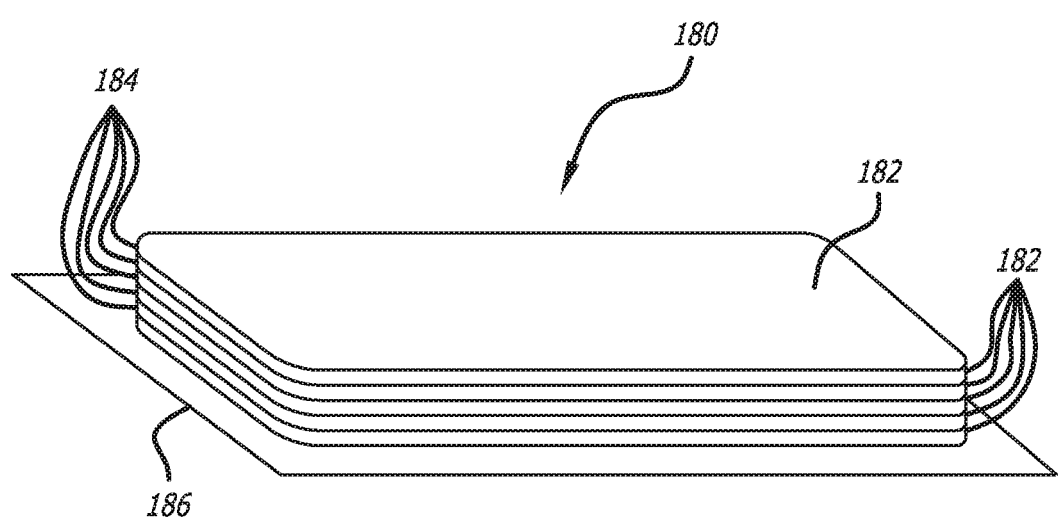
FIG. 14 is a perspective view of an embodiment of a gel tab of the invention; and, FIG. 15 is a side elevation of an embodiment of a CPAP mask of the invention.

One embodiment 180 of an evaporative device is shown in FIG. 14. This device is a gel tab consisting of a plurality of odorant layers 182 separated by odorless layers 184. In this example there are six odorant layers 182 separated by five odorless layers. The odorant layers are designed to evaporate at a desired rate such that each odorant layer represents an interval 30. The odorless layers are designed to evaporate at a desired rate such that each odorless layer represents a break 40. The desired timing of each layer may be controlled by the thickness of the layer during the manufacturing process. The odorless layers 184 would then be thinner than the odorant layers 182. The gel tabs 180 are provided on a substrate 186 such that only the top layer evaporates.

The gel tab 180 provides a base for a variety of delivery mechanisms encompassed in the invention. Additionally, it is envisioned that the gel tab 180 could shaped such that it may be removed from the substrate 186 and applied like tap directly to the upper lip or chin of the recipient. In this embodiment, it may be desired to include a odorless layer 184 as the top layer such that the user has a few minutes to fall asleep prior to experiencing the odorants.

Figure 15:
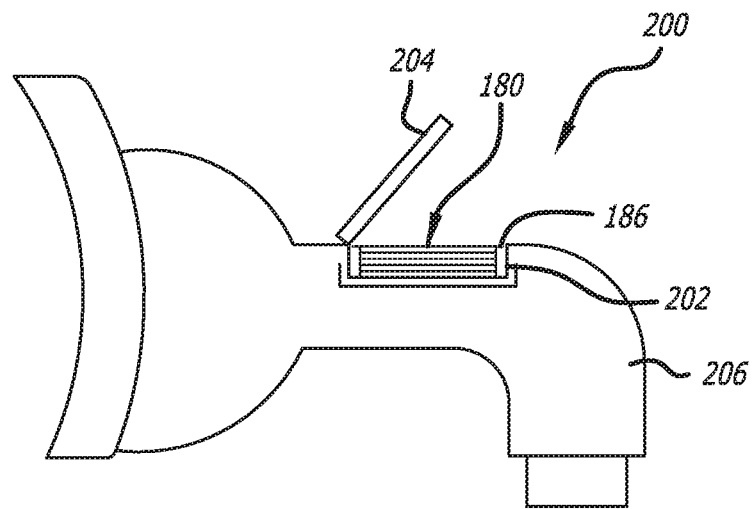

FIG. 15 shows a CPAP mask 200 that has been modified slightly to accommodate a gel tab 180. The mask 200 has a nozzle 206 that connects to the gas delivery tube of a typical CPAP machine (not shown). The nozzle 206 includes a compartment 202 with a lid 204 that can be opened so that a gel tab 180 may be placed therein. The tab 180 is placed such that the substrate 186 is on the top. During use, the gas flowing through the nozzle 206 from the CPAP machine passes under the bottom, exposed layer of the tab 180 and is inhaled by the user. In the morning, the empty substrate 186 is discarded.

Other devices are envisioned that utilize the gel tab 180 including, but not limited to, plug-in style air fresheners, non-CPAP masks, pendants and other wearable devices, nose plugs, heat-activated devices, diffusers, etc.

EXAMPLES

The following examples are presented to illustrate the present invention and to assist one of ordinary skill in making and using the same. The examples are not intended in any way to otherwise limit the scope of the invention.

Example 1: Environmental Enrichment in Inner-City Classrooms

This Example demonstrates enhancing brain responses with multiple olfactory stimulation in school children. Children in an inner-city school were exposed to 30 minutes of olfactory stimulation daily in the classroom using essential oil fragrances, one per day, rotating through 5 different scents (n=25 children), for 3 months. Another group of 23 children was left without such stimulation, serving as controls. Stroop test scores were monitored over that period. This test assesses cognitive processing speed, attention capacity, and executive function. In addition, the Stroop test has a strong correlation with IQ, general behavior, and school performance (Imbrosciano and Berlach, 2005).

Figure 16:
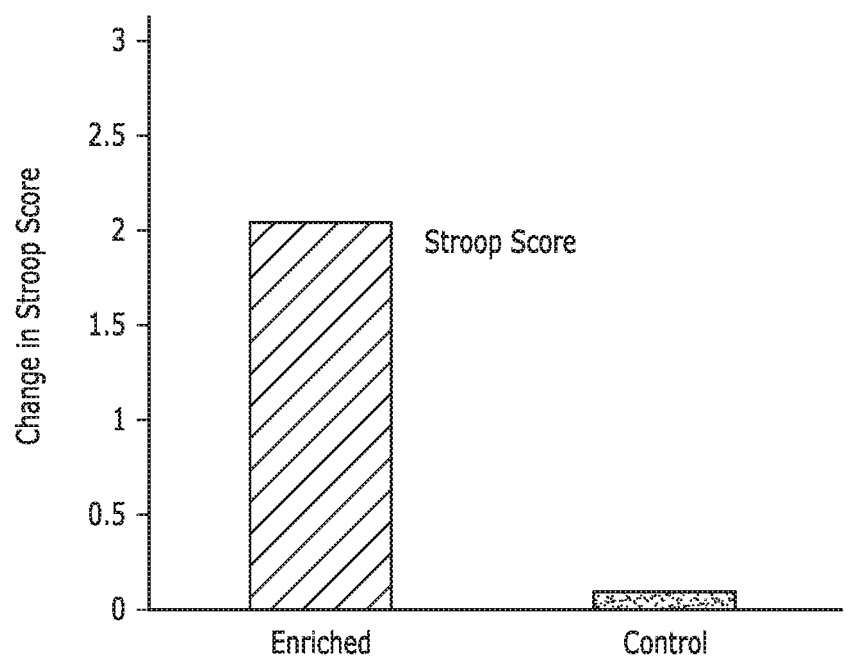
FIG. 16 is a graph showing a change in Stroop score using the invention.

As shown in FIG. 16, olfactory-enriched children had more than 10 times the improvement observed in controls on that test. The classes were team taught by the same teachers, making it unlikely that this phenomenon was due to differences in the teaching ability of their teachers. While there have been many attempts to improve cognitive outcomes for children in elementary school, such attempts have generally been unsuccessful in increasing their cognitive capacity.

Example 2: Environmental Enrichment for Older Adults

This Example demonstrates the positive impact of olfactory stimulation on the cognitive ability of older adults. The older adults were tested using standard, validated cognitive assessments, and then retested after they had received daily olfactory stimulation. The stimulated older adults had improvements that were 181%, 268% and 1,258% better than controls.

Older adults were given a set of pleasant scents and asked to expose themselves to the scents using a provided nebulizer for 30 min in the morning and 30 min in the evening every day for 6 months. 40 older adults (60-75 years old) gave themselves patterned olfactory stimulation at home, or were assigned to a group that did not experience increased olfactory stimulation. Three tests of cognition were administered at the start of the trial, and then again after 6 months.

Figure 17:
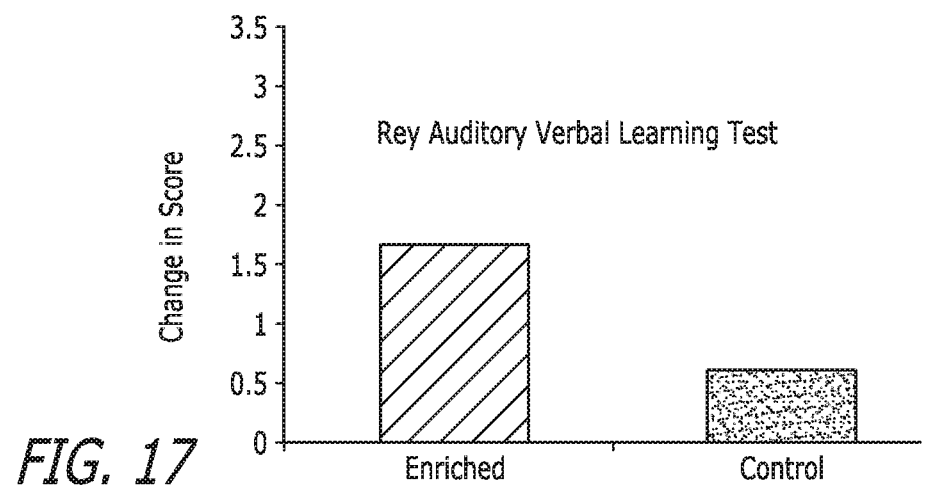
FIG. 17 is a graph showing a change in Rey Auditory Verbal Learning Test score using the invention.
Figure 18:
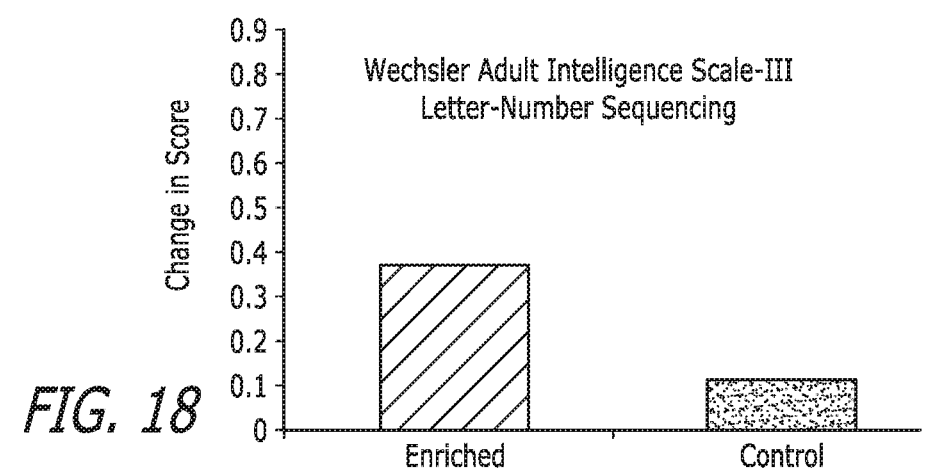
FIG. 18 is a graph showing a change in Wechsler Adult Intelligence Scale-Ill-Letter-Number Sequencing score using the invention; and, FIG. 19 is a graph showing a change in Wechsler Adult Intelligence Scale-III Backwards Digit Span score using the invention.
Figure 19:
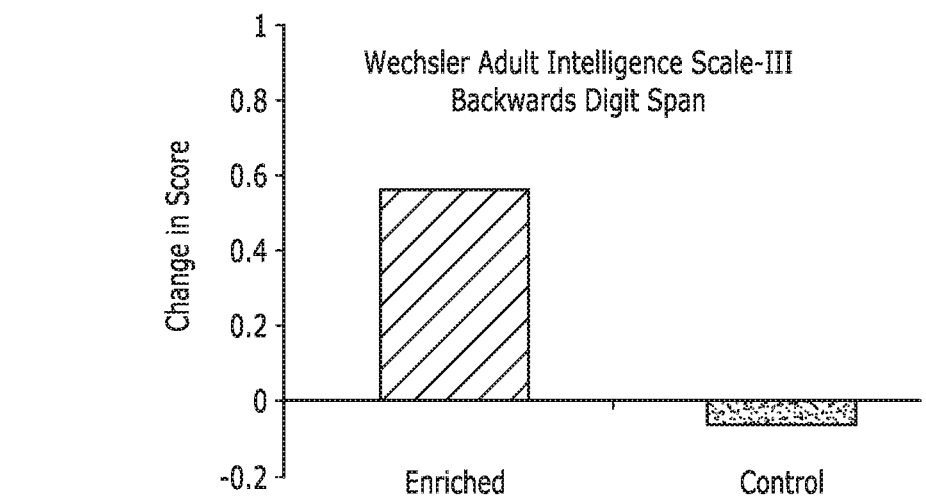

In a test that reveals verbal learning and memory (Rey Auditory Verbal Learning), olfactory-enriched older adults performed 181% better than controls (FIG. 17). In a test of sequential processing, mental manipulation, attention, concentration, memory span, and short-term auditory memory (WAIS III Letter-Number Sequencing), the enriched group had a 268% advantage over controls (FIG. 18). Finally, in a test of rote learning and memory, attention, encoding, and auditory processing, working memory, transformation of information, mental manipulation, and visual-spatial imaging (WAIS III Backwards Digit Span), the enriched group performed 1,258% better than controls (FIG. 19).

These cognitive benefits are about 1-2 orders of magnitude better than computer games, direct brain stimulation, exercise or social interactions (Clemenson and Stark, 2015; Ezzyat, et al., 2018; Hertzog, et al. 2009; Kirk-Sanchez and McGough, 2014; Kucewisc, et al., 2018).

REFERENCES

Adams D R, Kern D W, Wroblewski K E, McClintock M K, Dale W, Pinto J M. (2018). Olfactory dysfunction predicts subsequent dementia in older U.S. adults. J Am Geriatr Soc. 66:140-144.

Altundag A, Cayonu M, Kayabasoglu G, Salihoglu M, Tekeli H, Saglam O, Hummel T. (2015), Modified olfactory training in patients with postinfectious olfactory loss. Laryngoscope. 125:1763-1766.

Arendash G W, Garcia M F, Costa D A, Cracchiolo J R, Wefes I M, Potter H. (2004). Environmental enrichment improves cognition in aged Alzheimer's transgenic mice despite stable beta-amyloid deposition. Neuroreport. 15:1751-1754.

Aronoff E, Hillyer R, Leon M. (2016). Environmental enrichment therapy for autism: outcomes with increased access. Neural Plasticity, vol. 2016, Article ID 2734915, 23 pages.

Arranz L, De Castro N M, Baeza I, Giménez-Llort L, De la Fuente M. (2011). Effect of environmental enrichment on the immunoendocrine aging of male and female triple-transgenic 3xTg-A D mice for Alzheimer's disease. J Alzheimer's Dis. 25:727-737.

Basak C, Boot W R, Voss M W, Kramer A F. (2008). Can training in a real-time strategy videogame attenuate cognitive decline in older adults? Psychol Aging. 23: 765-777.

Berardi N, Braschi C, Capsoni S, Cattaneo A, Maffei L. (2007). Environmental enrichment delays the onset of memory deficits and reduces neuropathological hallmarks in a mouse model of Alzheimer-like neurodegeneration. J Alzheimers Dis. 11:359-370.

Bitter T, Brüderlea J, Gudziol H, Hartmut Peter Burmeister H P, Gaser C, Guntinas-Lichius O. (2010b). Gray and white matter reduction in hyposmic subjects—A voxel-based morphometry study. Brain Res. 1347:42-47.

Bitter T, Gudziol H, Burmeister H P, Mentzel H-J, Guntinas-Lichius O, Gaser C. (2010a). Anosmia leads to a loss of gray matter in cortical brain areas. Chem Senses 35:407-415.

Bitter T, Siegert F, Gudziol H, Burmeister H P, Mentzel H J, Hummel T, Gaser C, Guntinas-Lichius O. (2011). Gray matter alterations in parosmia. Neuroscience. 177:177-182.

Boudjarane M A, Grandgeorge M, Marianowski R, Misery L, Lemonnier É. (2017). Perception of odors and tastes in autism spectrum disorders: A systematic review of assessments. Autism Res. 10:1045-1057.

Choi J S, Hur K, Chow M, Shen J, Wrobel B. (2018). Olfactory dysfunction and cognition among older adults in the United States. Int Forum Allergy Rhinol. [Epub ahead of print]

Conti M Z, Vicini-Chilovi B, Riva M, Zanetti M, Liberini P, Padovani A, Rozzini L. Odor identification deficit predicts clinical conversion from mild cognitive impairment to dementia due to Alzheimer's disease. Arch Clin Neuropsychol. 28:391-399.

Clemenson G D, Stark C E L. (2015). Virtual environmental enrichment through video games improves hippocampal-associated memory. J. Neurosci. 35:16116-16125.

Costa D A, Cracchiolo J R, Bachstetter A D, Hughes T F, Bales K R, Paul S M, Mervis R F, Arendash G W, Potter H. (2007). Enrichment improves cognition in A D mice by amyloid-related and unrelated mechanisms. Neurobiol Aging. 28:831-844.

Damm M, Pikart L K, Reimann H, Burkert S, Göktas Ö, Haxel B, Frey S, Charalampakis I, Beule A, Renner B, Hummel T, Hüttenbrink K B. (2014). Olfactory training is helpful in postinfectious olfactory loss: a randomized, controlled, multicenter study. Laryngoscope. 124:826-831.

Devanand D P, Michaels-Marston K S, Liu X, Pelton G H, Padilla M, Marder K, Bell K, Stern Y, Mayeux R. (2000). Olfactory deficits in patients with mild cognitive impairment predict Alzheimer's disease at follow-up. Am J Psychiatry. 157:1399-1405.

Devanand D P, Tabert M H, Cuasay K, Manly J J, Schupf N, Brickman A M, Andrews H, Brown T R, DeCarli C, Mayeux R. (2010). Olfactory identification deficits and MCI in a multi-ethnic elderly community sample. Neurobiol Aging. 31:1593-600.

Dong J, Pinto J M, Guo X, Alonso A, Tranah G, Cauley J A, Melissa Garcia, Satterfield S, Huang X, Harris T, Mosley T H, Chen H. (2017). The prevalence of anosmia and associated factors among U.S. black and white older adults. J Gerontol A Biol Sci Med Sci. 72:1080-1086.

Doty R L, Deems D A, Stellar S. (1988). Olfactory dysfunction in Parkinsonism: a general deficit unrelated to neurologic signs, disease stage, or disease duration. Neurology. 38:1237-1244.

Doty R L, Shaman P, Applebaum S L, Giberson R, Siksorski L, Rosenberg L. (1984). Smell identification ability: changes with age. Science. 226:1441-1443.

Endevelt-Shapira Y, Perl O, Ravia A, Amir D, Eisen A, Bezalel V, Rozenkrantz L, Mishor E, Pinchover L, Soroka T, Honigstein D, Sobel N. (2018). Altered responses to social chemosignals in autism spectrum disorder. Nat Neurosci. 21:111-119.

Ezzyat Y, Wanda P A, Levy D F, Kadel A, Aka A, Pedisich I, Sperling M R, Sharan A D, Lega B C, Burks A, Gross R E, Inman C S, Jobst B C, Gorenstein M A, Davis K A, Worrell G A, Kucewicz M T, Stein J M, Gorniak R, Das S R, Rizzuto D S, Kahana M J. (2018). Closed-loop stimulation of temporal cortex rescues functional networks and improves memory. Nat Commun. 9:365.

Geißler K, Reimann H, Gudziol H, Bitter T, Guntinas-Lichius O. (2014). Olfactory training for patients with olfactory loss after upper respiratory tract infections. Eur Arch Otorhinolaryngol. 271:1557-1562.

Gopinath B, Sue C M, Kifley A, Mitchell P. (2012). The association between olfactory impairment and total mortality in older adults. J Gerontol. Series A, 67A:204-209.

Haehner A, Tosch C, Wolz M, Klingelhoefer L, Fauser M, Storch, A, Reichmann H, Hummel T. (2013) Olfactory training in patients with Parkinson's disease. PLoS ONE. 8:e61680.

Hertzog C, Kramer A F, Wilson R S, Lindenberger U. (2008) Enrichment effects on adult cognitive development: can the functional capacity of older adults be preserved and enhanced? Psychol Sci Public Interest. 9:1-65.

Hoffman H J, Rawal S, Li C-M, Duffy V B. (2016). New chemosensory component in the U.S. National Health and Nutrition Examination Survey (NHANES): first-year results for measured olfactory dysfunction. Rev Endocr Metab Disord. 17:221-240

Hoffmann K, Sobol N A, Frederiksena K S, Beyerb N, Vogela A, Vestergaardd K, Brændgaarde H, Gottrupe H, Lolkf A, Wermuthf L, Jacobseng S, Laugesenh L P, Gergelyffyh R G, Høghi P, Bjerregaardj E, Andersena B B, Siersmak V, Johannsena P, Cotman C W, Waldemara G, Hasselbalcha S G. (2016). Moderate-to-high intensity physical exercise in patients with Alzheimer's disease: a randomized controlled trial. J Alzheimers Dis. 50:443-453.

Hummel T, Rissom K, Reden J, Hähner A, Weidenbecher M, Hüttenbrink K-B. (2009), Effects of olfactory training in patients with olfactory loss. Laryngoscope. 119:496-499.

Jankowsky J L, Melnikova T, Fadale D J, Xu G M, Slunt H H, Gonzales V, Younkin L H, Younkin S G, Borchelt D R, Savonenko A V. (2005). Environmental enrichment mitigates cognitive deficits in a mouse model of Alzheimer's disease. J Neurosci. 25:5217-5224.

Kerr B, Silva P A, Walz K, Young J I. (2010). Unconventional transcriptional response to environmental enrichment in a mouse model of Rett syndrome. PLoS ONE. 5, e11534.

Kirk-Sanchez N J, McGough E L. (2014). Physical exercise and cognitive performance in the elderly: current perspectives. Clin Interven Aging. 9:51-62.

Klimova B. (2016). Computer-based cognitive training in aging. Front Aging Neurosci. 8:313.

Kollndorfer K, Jakab A, Mueller C, Trattnig S, Schopf V. (2015). Effects of chronic peripheral olfactory loss on functional brain networks. Neuroscience. 310:589-599.

Kondo M, Gray L J, Pelka G J, Christodoulou J, Tam P P, Hannan A J. (2008). Environmental enrichment ameliorates a motor coordination deficit in a mouse model of Rett syndrome-Mecp2 gene dosage effects and BDNF expression. Eur J Neurosci. 27, 3342-3350.

Konstantinidis I, Tsakiropoulou E, Bekiaridou P, Kazantzidou C, Constantinidis J. (2013). Use of olfactory training in post-traumatic and postinfectious olfactory dysfunction. Laryngoscope. E85-E90.

Konstantinidis I, Tsakiropoulou E, Constantinidis J. (2016). Long term effects of olfactory training in patients with postinfectious olfactory loss. Laryngoscope. 54: 170-175.

Kucewicz M T, Berry B M, Miller L R, Khadjevand F, Ezzyat Y, Stein J M, Kremen V, Brinkmann B H, Wanda P, Sperling M R, Gorniak R, Davis K A, Jobst B C, Gross R E, Lega B, Van Gompel J, Stead S M, Rizzuto D S, Kahana M J, Worrell G A. (2018). Evidence for verbal memory enhancement with electrical brain stimulation in the lateral temporal cortex. Brain. [Epub ahead of print]

Lacaria M, Spencer C, Gu W, Paylor R, Lupski J R. (2012). Enriched rearing improves behavioral responses of an animal model for CNV-based autistic-like traits. Human Mol Genet. 21, 3083-3096.

Lafaille-Magnan M-E, Poirier J, Etienne P, Tremblay-Mercier J, Frenette J, Rosa-Neto P, Breitner J C S, for the PREVENT-AD Research Group. (2017). Odor identification as a biomarker of preclinical AD in older adults at risk. Neurology. 89:327-335.

Lazarov O, Robinson J, Tang Y P, Hairston I S, Korade-Mirnics Z, Lee V M, Hersh L B, Sapolsky R M, Mimics K, Sisodia S S. (2005). Environmental enrichment reduces Abeta levels and amyloid deposition in transgenic mice. Cell. 120:701-713.

Li W, Howard J D, Gottfried J A. (2010). Disruption of odour quality coding in piriform cortex mediates olfactory deficits in Alzheimer's disease. Brain. 133:2714-2726.

Liu G, Zong G, Doty R L, Sun Q. (2016). Prevalence and risk factors of taste and smell impairment in a nationwide representative sample of the US population: a cross-sectional study. BMJ Open. 6:e013246.

Lonetti G, Angelucci A, Morando L, Boggio E M, Giustetto M, Pizzorusso T. (2010). Early environmental enrichment moderates the behavioral and synaptic phenotype of MeCP2 null mice. Biol Psychiatry. 67, 657-665.

Luzzi S, Snowden J S, Neary D, Coccia M, Provinciali L, Lambon Ralph M A (2007) Distinct patterns of olfactory impairment in Alzheimer's disease, semantic dementia, frontotemporal dementia, and corticobasal degeneration. Neuropsychologia. 45:1823-1831.

Meusel T, Westermann B, Fuhr P, Hummel T, Welge-Lüssen A. (2010). The course of olfactory deficits in patients with Parkinson's disease—a study based on psychophysical and electrophysiological measures. Neurosci Lett. 486: 166-170.

Murphy C, Schubert C R, Cruickshanks K J, Klein B E, Klein R, Nondahl D M. (2002). Prevalence of olfactory impairment in older adults. JAMA. 288:2307-2312.

Nag N, Moriuchi J M, Peitzman C G, Ward B C, Kolodny N H, Berger-Sweeney J E. (2009). Environmental enrichment alters locomotor behaviour and ventricular volume in Mecp2 1lox mice. Behav Brain Res. 196, 44-48.

Nguyen A D, Shenton M E, Levitt J J. (2010). Olfactory dysfunction in schizophrenia: a review of neuroanatomy and psychophysiological measurements. Harv Rev Psychiatry. 18:279-292.

Park H L, O'Connell J E, Thomson R G. (2003). A systematic review of cognitive decline in the general elderly population. Int J Geriatr Psychiatry. 18:1121-1134.

Parrao T, Chana P, Venegas P, Behrens M I, Aylwin M L. (2012). Olfactory deficits and cognitive dysfunction in Parkinson's disease. Neurodegener Dis. 10:179-182.

Patel T R (2012). Environmental enrichment: aging and memory. Yale J Biol Med. 85:491-500.

Patel Z M, Wise S K, DelGaudio J M. (2017). Randomized controlled trial demonstrating cost-effective method of olfactory training in clinical practice: essential oils at uncontrolled concentration. Laryngoscope Invest Otolaryngol. 2:53-56.

Peters J M, Hummel T, Kratzsch T, Lötsch J, Skarke C, Frölich L. (2003). Olfactory function in mild cognitive impairment and Alzheimer's disease: an investigation using psychophysical and electrophysiological techniques. Am J Psychiatry. 160:1995-2002.

Pinto J M, Wroblewski K E, Kern D W, Schumm L P, McClintock M K. (2015). The rate of age-related olfactory decline among the general population of older U.S. adults. J Gerontol A, Biol Sci Med Sci. 70:1435-1441.

Pinto J M, Wroblewski K E, Kern D W, Schumm L P, McClintock M K (2014). Olfactory dysfunction predicts 5-year mortality in older adults. PLoS ONE. 9:e107541.

Polito L, Chierchia A, Tunesi M, Bouybayoune I, Kehoe P G, Albani D, Forloni G. (2014). Environmental enrichment lessens cognitive decline in app23 mice without affecting brain sirtuin expression. J Alzheimer's Dis. 42:851-864.

Ponsen M M, Stoffers D, Booij J, van Eck-Smit B L, Wolters E C, Berendse H W. (2004). Idiopathic hyposmia as a preclinical sign of Parkinson's disease. Ann Neurol. 56:173-181.

Restivo L, Ferrari F, Passino E, Sgobio C, Bock J, Oostra B A., Bagni C, Ammassari-Teule M. (2005). Enriched environment promotes behavioral and morphological recovery in a mouse model for the fragile X syndrome. Proc Nat Acad Sci. USA. 102:11557-11562.

Reynolds S, Urruela M, Devine D P. (2013). Effects of environmental enrichment on repetitive behaviors in the BTBR T_tf/J mouse model of autism. Autism Res. 6, 337-343.

Roberts R O, Christianson T, J H, Kremers W K, Mielke M M, Machulda M M, Vassilaki M, Alhurani R E, Geda Y E, Knopman D S, Petersen R C. (2016). Association between olfactory dysfunction and amnestic mild cognitive impairment and Alzheimer disease dementia. JAMA Neurol. 73:93-101.

Rodakowski J, Saghafi E, Butters M A, Skidmore E R. (2015). Non-pharmacological Interventions for Adults with Mild Cognitive Impairment and Early Stage Dementia: An Updated Scoping Review. Mol Aspects Med. 0, 38-53.

Ross G W, Abbott R D, Petrovitch H, Tanner C M, Davis D G, Nelson J, Markesbery W R, Hardman J, Masaki K, Launer L, White L R. (2006). Association of olfactory dysfunction with incidental Lewy bodies. Mov Disord. 21:2062-2067.

Rozenkrantz L, Zachor D, Heller I, Plotkin A, Weissbrod A, Snitz K, Secundo L, Sobel N. (2015). A mechanistic link between olfaction and autism spectrum disorder. Curr Biol. 25:1904-1910.

Sakamoto Y, Ebihara S, Ebihara T, Tomita N, Toba K, Freeman S, Arai H, Kohzuki M. (2012). Fall prevention using olfactory stimulation with lavender odor in elderly nursing home residents, a randomized controlled trial. J Am Geriatr Soc. 60:1005-1011.

Salthouse T A. (2009). When does age-related cognitive decline begin? Neurobiol Aging. 30:507-514.

Schneider T, Turczak, J, Przewlocki R. (2006). Environmental enrichment reverses behavioral alterations in rats prenatally exposed to valproic acid: Issues for a therapeutic approach in autism. Neuropsychopharmacology. 31, 36-46.

Schubert C R, Carmichael L L, Murphy C, Klein B E K, Klein R, Cruickshanks K J. (2008). Olfaction and the 5-year incidence of cognitive impairment in an epidemiologic study of older adults. J Am Geriatrics Soc. 56:1517-1521.

Schubert C R, Fischer M E, Pinto A A, Klein B E K, Klein R, Cruickshanks K J. (2017). Odor detection thresholds in a population of older adults. Laryngoscope. 127: 1257-1262.

Segovia G, Yague A G, Garcia-Verdugo J M, Mora F. (2006). Environmental enrichment promotes neurogenesis and changes the extracellular concentrations of glutamate and GABA in the hippocampus of aged rats. Brain Res Bull. 70:8-14.

Segura B, Baggio H C, Solanaa, E, Palacios E M, Vendrell P, Bargalló N, Junquéa C. (2013). Neuroanatomical correlates of olfactory loss in normal aged subjects. Behav Brain Res. 246:148-153.

Seubert J J, Laukka E J, Rizzuto D, Hummel T, Fratiglioni L, Bäckman L, Larsson M. (2017). Prevalence and correlates of olfactory dysfunction in old age: a population-based study. J Gerontol A Biol Sci Med Sci. 72:1072-1079.

Sohrabi H R, Bates K A, Weinborn M G, Johnston A N B, Bahramian A, Taddei, K, Laws S M, Rodrigues M, Morici M, Howard M, Martins G, Mackay-Sim A, Gandy S E, Martins R N. (2012). Olfactory discrimination predicts cognitive decline among community-dwelling older adults. Transl Psychiatry. 2, e118-.

Swan G E, Carmelli D. (2002). Impaired olfaction predicts cognitive decline in nondemented older adults. Neuroepidemiology. 21:58-67.

Tabaton M, Monaco S, Cordone M P, Colucci M, Giaccone G, Tagliavini F, Zanusso G. (2004). Prion deposition in olfactory biopsy of sporadic Creutzfeldt-Jakob disease. Ann Neurol. 55:294-296.

Tonacci A, Billeci L, Tartarisco G, Ruta L, Muratori F, Pioggia G, Gangemi S. (2017). Olfaction in autism spectrum disorders: A systematic review. Child Neuropsychol. 23:1-25.

Toussaint N, de Roon M, van Campen J P, Kremer S, Boesveldt S. (2015). Loss of olfactory function and nutritional status in vital older adults and geriatric patients. Chem Senses. 40:197-203.

Valero J, España J, Parra-Damas A, Martin E, Rodríguez-Álvarez J, Saura C A (2011). Short-term environmental enrichment rescues adult neurogenesis and memory deficits in app (sw,ind) transgenic mice. PLoS ONE. 6:e16832.

Wattendorf E, Welge-Lüssen A, Fiedler K, Bilecen D, Wolfensberger M, Fuhr P, Hummel T, Westermann B. (2009). Olfactory impairment predicts brain atrophy in Parkinson's disease. J Neurosci. 29:15410-15413.

Wegener B A, Croy I, Hähner A, Hummel T. (2018). Olfactory training with older people. Int J Geriatr Psychiatry. 33:212-220.

Williams K, Kemper S. (2010). Exploring interventions to reduce cognitive decline in aging. J Psychosoc Nurs Ment Health Serv. 48:42-51.

Williams N H, Hendry M, France B, Lewis R, Wilkinson C. (2007). Effectiveness of exercise-referral schemes to promote physical activity in adults: systematic review. Brit J Gen Practice. 57:979-986.

Woo C C, Donnelly J H, Steinberg-Epstein R, Leon M. (2015). Environmental enrichment as a therapy for autism: A clinical trial replication and extension. Behav Neurosci. 129:412-422.

Woo C C, Leon M. (2013). Environmental enrichment as an effective treatment for autism: A randomized controlled trial. Behav Neurosci. 127:487-497.

Yao L, Pinto J M, Yi X, Li L, Peng P, Wei Y. (2014). Gray matter volume reduction of olfactory cortices in patients with idiopathic olfactory loss. Chem Senses. 39:755-760.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of improving far transfer effects of cognition of a human comprising:
    establishing a 24-hour treatment schedule including a plurality of intervals separated by breaks;
    inputting the 24-hour treatment schedule into a scent-delivery device such that the device delivers one of a plurality of scents during each interval, and stops the delivery of the scent at the end of the interval;
    ensuring that scents delivered during consecutive intervals are sufficiently distinct from each other so as to be distinguished by said human;
    ensuring that no scent is repeated more than once during the 24-hour treatment schedule; and
    repeating the 24-hour treatment schedule each day for a predetermined treatment length while varying the scents delivered from said plurality of scents.

2. The method of claim 1 wherein establishing the 24-hour treatment schedule including the plurality of intervals separated by breaks comprises scheduling a plurality of 30 minute intervals separated by 5 minute breaks.

3. The method of claim 1 wherein establishing the 24-hour treatment schedule including the plurality of intervals separated by breaks comprises scheduling at least three intervals separated by breaks.

4. The method of claim 1 wherein inputting the 24-hour treatment schedule into a scent-delivery device comprises wirelessly connecting the device to a handheld electronic device having an application that allows the schedule to be uploaded to the scent-delivery device.

5. The method of claim 1 wherein inputting the 24-hour treatment schedule into a scent-delivery device comprises setting a start time.

6. The method of claim 1 wherein establishing a 24-hour treatment schedule comprises basing an initiation of the schedule on an activity signifying that a user is going to bed.

7. The method of claim 6 wherein said activity comprises plugging a handheld device into the scent-delivery device.

8. The method of claim 7 wherein said activity comprises a biometric sensor, wirelessly connected to the hand-held device, providing data that indicates the user has begun a sleep-cycle.

9. A method of improving far transfer effects of cognition of a human comprising:
    providing a programmable scent-delivery device capable of delivering a plurality of distinct scents, one at a time, based on a 24-hr treatment schedule programmed into the device having intervals separated by breaks;
    selecting scents to comprise said plurality of distinct scents that may be unfamiliar to the human; activating the device in the presence of the human such that an initial exposure to said selected scents occur while the human is sleeping;
    ensuring that scents delivered during consecutive intervals are sufficiently distinct from each other so as to be distinguished, consciously or unconsciously, by said human; and
    repeating the activation step and the ensuring step on subsequent days for a predetermined treatment length using the same or different scents.

10. The method of claim 9 further comprising ensuring that no scent is repeated more than once during the 24-hour treatment schedule.

11. The method of claim 9 wherein an order said scents are delivered from said plurality of scents is otherwise random so long as said ensuring step is satisfied.

* * * * *